US010429391B2

(12) United States Patent
Sitek et al.

(10) Patent No.: US 10,429,391 B2
(45) Date of Patent: Oct. 1, 2019

(54) BIOMARKERS FOR CHOLANGIOCELLULAR CARCINOMA (CCC)

(71) Applicant: LEIBNIZ-INSTITUT FÜR ANALYTISCHE WISSENSCHAFTEN—ISAS—E.V., Dortmund (DE)

(72) Inventors: Barbara Sitek, Witten (DE); Helmut E. Meyer, Recklinghausen (DE); Dominik Megger, Dortmund (DE); Thilo Bracht, Bochum (DE); Juliet Padden, Bochum (DE); Hideo A. Baba, Essen (DE); Jörg F. Schlaak, Essen (DE); Frank Weber, Essen (DE)

(73) Assignee: LEIBNIZ-INSTITUT FÜR ANALYTISCHE WISSENSCHAFTEN—ISAS—E.V., Dortmund (DE)

( * ) Notice: Subject to any disclaimer, the term of this patent is extended or adjusted under 35 U.S.C. 154(b) by 309 days.

(21) Appl. No.: 14/916,583

(22) PCT Filed: Sep. 8, 2014

(86) PCT No.: PCT/EP2014/069115
§ 371 (c)(1),
(2) Date: Mar. 4, 2016

(87) PCT Pub. No.: WO2015/032954
PCT Pub. Date: Mar. 12, 2015

(65) Prior Publication Data
US 2016/0195537 A1   Jul. 7, 2016

(30) Foreign Application Priority Data
Sep. 6, 2013   (EP) .................................... 13183452

(51) Int. Cl.
 G01N 31/00   (2006.01)
 G01N 33/574  (2006.01)
 G01N 33/68   (2006.01)
 G01N 33/53   (2006.01)

(52) U.S. Cl.
CPC . G01N 33/57446 (2013.01); G01N 33/57438 (2013.01); G01N 33/6848 (2013.01); G01N 2500/04 (2013.01); G01N 2560/00 (2013.01); G01N 2570/00 (2013.01); G01N 2800/52 (2013.01)

(58) Field of Classification Search
None
See application file for complete search history.

(56) References Cited

U.S. PATENT DOCUMENTS

2014/0027283 A1   1/2014 Mischak

FOREIGN PATENT DOCUMENTS

WO   WO-2012076723 A1   6/2012

OTHER PUBLICATIONS

Darby et al. (Cancer Microenvironment, vol. 4, No. 1, 2011, pp. 73-91).*
International Search Report for PCT/EP2014/069115 dated Apr. 1, 2015.
Darby, I., et al., "Proteomic Analysis of Differentially Expressed Proteins in Peripheral Cholangiocarcinoma", Cancer Microenvironment, vol. 4, No. 1, 2011, pp. 73-91.
Kawase, H., et al., "Differential LC-MS-Based Proteomics of Surgical Human Cholangiocarcinoma Tissues", Journal of Proteome Research, vol. 8, No. 8, 2009, pp. 4092-4103.
Padden, J., et al., "Identification of Novel Biomarker Candidates for the Immunohistochemical Diagnosis of Cholangiocellular Carcinoma", Molecular & Cellular Proteomics, vol. 13, No. 10, 2014, pp. 2661-2672.
Padden, J., et al., "A Proteomic Study of Cholangiocellular Carcinoma for Detection of Novel Biomarkers in the Bile", Journal of Hepatology, vol. 58, Suppl. 1, 2013, Article No. 1068, p. S438.
Megger, D. A., et al., "Proteomic Differences Between Hepatocellular Carcinoma and Nontumorous Liver Tissue Investigated by a Combined Gel-Based and Label-Free Quantitative Proteomics Study", Molecular & Cellular Proteomics, 2013, vol. 12.7, pp. 2006-2020.
International Preliminary Report on Patentability for PCT/EP2014/069115 dated Mar. 8, 2016.

* cited by examiner

Primary Examiner — Lisa V Cook
(74) Attorney, Agent, or Firm — Drinker Biddle & Reath LLP

(57) ABSTRACT

The invention relates to a method for identifying specific marker proteins (biomarkers) for cholangiocellular carcinoma (CCC), the biomarkers for CCC identified by the method and the use thereof, in particular for diagnosis, surveillance and treatment. The invention further relates to a diagnostic device comprising the biomarkers for CCC and a screening assay wherein these biomarkers for CCC are used to identify novel pharmaceutical compounds for treatment of CCC.

4 Claims, 5 Drawing Sheets

Figure 1:
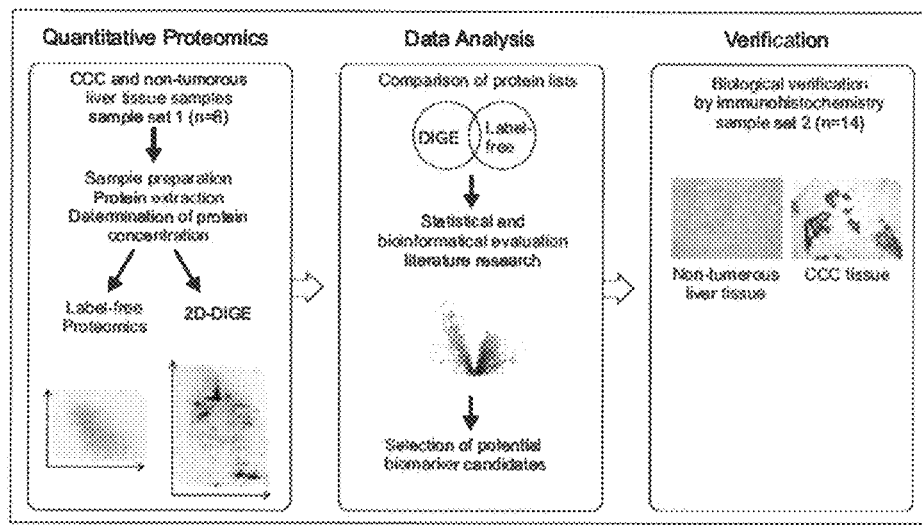

Specification includes a Sequence Listing.

SEQUENCE LISTING

```
<160> NUMBER OF SEQ ID NOS: 15

<210> SEQ ID NO 1
<211> LENGTH: 240
<212> TYPE: PRT
<213> ORGANISM: Homo sapiens

<400> SEQUENCE: 1

Met Ala Glu Glu Gln Pro Gln Val Glu Leu Phe Val Lys Ala Gly Ser
1               5                   10                  15

Asp Gly Ala Lys Ile Gly Asn Cys Pro Phe Ser Gln Arg Leu Phe Met
            20                  25                  30

Val Leu Trp Leu Lys Gly Val Thr Phe Asn Val Thr Thr Val Asp Thr
        35                  40                  45

Lys Arg Arg Thr Glu Thr Val Gln Lys Leu Cys Pro Gly Gly Gln Leu
    50                  55                  60

Pro Phe Leu Leu Tyr Gly Thr Glu Val His Thr Asp Thr Asn Lys Ile
65                  70                  75                  80

Glu Glu Phe Leu Glu Ala Val Leu Cys Pro Pro Arg Tyr Pro Lys Leu
                85                  90                  95

Ala Ala Leu Asn Pro Glu Ser Asn Thr Ala Gly Leu Asp Ile Phe Ala
            100                 105                 110

Lys Phe Ser Ala Tyr Ile Lys Asn Ser Asn Pro Ala Leu Asn Asp Asn
        115                 120                 125

Leu Glu Lys Gly Leu Leu Lys Ala Leu Lys Val Leu Asp Asn Tyr Leu
    130                 135                 140

Thr Ser Pro Leu Pro Glu Glu Val Asp Glu Thr Ser Ala Glu Asp Glu
145                 150                 155                 160

Gly Val Ser Gln Arg Lys Phe Leu Asp Gly Asn Glu Leu Thr Leu Ala
                165                 170                 175

Asp Cys Asn Leu Leu Pro Lys Leu His Ile Val Gln Val Val Cys Lys
            180                 185                 190

Lys Tyr Arg Gly Phe Thr Ile Pro Glu Ala Phe Arg Gly Val His Arg
        195                 200                 205

Tyr Leu Ser Asn Ala Tyr Ala Arg Glu Glu Phe Ala Ser Thr Cys Pro
    210                 215                 220
```

```
Asp Asp Glu Glu Ile Glu Leu Ala Tyr Glu Gln Val Ala Lys Ala Leu
225                 230                 235                 240

<210> SEQ ID NO 2
<211> LENGTH: 124
<212> TYPE: PRT
<213> ORGANISM: Homo sapiens

<400> SEQUENCE: 2

Met Ser Tyr Ile Pro Gly Gln Pro Val Thr Ala Val Val Gln Arg Val
1               5                   10                  15

Glu Ile His Lys Leu Arg Gln Gly Glu Asn Leu Ile Leu Gly Phe Ser
            20                  25                  30

Ile Gly Gly Gly Ile Asp Gln Asp Pro Ser Gln Asn Pro Phe Ser Glu
        35                  40                  45

Asp Lys Thr Asp Lys Gly Ile Tyr Val Thr Arg Val Ser Glu Gly Gly
    50                  55                  60

Pro Ala Glu Ile Ala Gly Leu Gln Ile Gly Asp Lys Ile Met Gln Val
65                  70                  75                  80

Asn Gly Trp Asp Met Thr Met Val Thr His Asp Gln Ala Arg Lys Arg
                85                  90                  95

Leu Thr Lys Arg Ser Glu Glu Val Val Arg Leu Leu Val Thr Arg Gln
            100                 105                 110

Ser Leu Gln Lys Ala Val Gln Gln Ser Met Leu Ser
        115                 120

<210> SEQ ID NO 3
<211> LENGTH: 782
<212> TYPE: PRT
<213> ORGANISM: Homo sapiens

<400> SEQUENCE: 3

Met Ala Pro His Arg Pro Ala Pro Ala Leu Leu Cys Ala Leu Ser Leu
1               5                   10                  15

Ala Leu Cys Ala Leu Ser Leu Pro Val Arg Ala Ala Thr Ala Ser Arg
            20                  25                  30

Gly Ala Ser Gln Ala Gly Ala Pro Gln Gly Arg Val Pro Glu Ala Arg
        35                  40                  45

Pro Asn Ser Met Val Val Glu His Pro Glu Phe Leu Lys Ala Gly Lys
    50                  55                  60

Glu Pro Gly Leu Gln Ile Trp Arg Val Glu Lys Phe Asp Leu Val Pro
65                  70                  75                  80

Val Pro Thr Asn Leu Tyr Gly Asp Phe Phe Thr Gly Asp Ala Tyr Val
                85                  90                  95

Ile Leu Lys Thr Val Gln Leu Arg Asn Gly Asn Leu Gln Tyr Asp Leu
            100                 105                 110

His Tyr Trp Leu Gly Asn Glu Cys Ser Gln Asp Glu Ser Gly Ala Ala
        115                 120                 125

Ala Ile Phe Thr Val Gln Leu Asp Asp Tyr Leu Asn Gly Arg Ala Val
    130                 135                 140

Gln His Arg Glu Val Gln Gly Phe Glu Ser Ala Thr Phe Leu Gly Tyr
145                 150                 155                 160

Phe Lys Ser Gly Leu Lys Tyr Lys Lys Gly Gly Val Ala Ser Gly Phe
                165                 170                 175

Lys His Val Val Pro Asn Glu Val Val Gln Arg Leu Phe Gln Val
            180                 185                 190
```

```
Lys Gly Arg Arg Val Val Arg Ala Thr Glu Val Pro Val Ser Trp Glu
            195                 200                 205

Ser Phe Asn Asn Gly Asp Cys Phe Ile Leu Asp Leu Gly Asn Asn Ile
        210                 215                 220

His Gln Trp Cys Gly Ser Asn Ser Asn Arg Tyr Glu Arg Leu Lys Ala
225                 230                 235                 240

Thr Gln Val Ser Lys Gly Ile Arg Asp Asn Glu Arg Ser Gly Arg Ala
                245                 250                 255

Arg Val His Val Ser Glu Glu Gly Thr Glu Pro Glu Ala Met Leu Gln
            260                 265                 270

Val Leu Gly Pro Lys Pro Ala Leu Pro Ala Gly Thr Glu Asp Thr Ala
        275                 280                 285

Lys Glu Asp Ala Ala Asn Arg Lys Leu Ala Lys Leu Tyr Lys Val Ser
    290                 295                 300

Asn Gly Ala Gly Thr Met Ser Val Ser Leu Val Ala Asp Glu Asn Pro
305                 310                 315                 320

Phe Ala Gln Gly Ala Leu Lys Ser Glu Asp Cys Phe Ile Leu Asp His
                325                 330                 335

Gly Lys Asp Gly Lys Ile Phe Val Trp Lys Gly Lys Gln Ala Asn Thr
            340                 345                 350

Glu Glu Arg Lys Ala Ala Leu Lys Thr Ala Ser Asp Phe Ile Thr Lys
        355                 360                 365

Met Asp Tyr Pro Lys Gln Thr Gln Val Ser Val Leu Pro Glu Gly Gly
    370                 375                 380

Glu Thr Pro Leu Phe Lys Gln Phe Phe Lys Asn Trp Arg Asp Pro Asp
385                 390                 395                 400

Gln Thr Asp Gly Leu Gly Leu Ser Tyr Leu Ser Ser His Ile Ala Asn
                405                 410                 415

Val Glu Arg Val Pro Phe Asp Ala Ala Thr Leu His Thr Ser Thr Ala
            420                 425                 430

Met Ala Ala Gln His Gly Met Asp Asp Asp Gly Thr Gly Gln Lys Gln
        435                 440                 445

Ile Trp Arg Ile Glu Gly Ser Asn Lys Val Pro Val Asp Pro Ala Thr
    450                 455                 460

Tyr Gly Gln Phe Tyr Gly Gly Asp Ser Tyr Ile Ile Leu Tyr Asn Tyr
465                 470                 475                 480

Arg His Gly Gly Arg Gln Gly Gln Ile Ile Tyr Asn Trp Gln Gly Ala
                485                 490                 495

Gln Ser Thr Gln Asp Glu Val Ala Ala Ser Ala Ile Leu Thr Ala Gln
            500                 505                 510

Leu Asp Glu Glu Leu Gly Gly Thr Pro Val Gln Ser Arg Val Val Gln
        515                 520                 525

Gly Lys Glu Pro Ala His Leu Met Ser Leu Phe Gly Gly Lys Pro Met
    530                 535                 540

Ile Ile Tyr Lys Gly Gly Thr Ser Arg Glu Gly Gly Gln Thr Ala Pro
545                 550                 555                 560

Ala Ser Thr Arg Leu Phe Gln Val Arg Ala Asn Ser Ala Gly Ala Thr
                565                 570                 575

Arg Ala Val Glu Val Leu Pro Lys Ala Gly Ala Leu Asn Ser Asn Asp
            580                 585                 590

Ala Phe Val Leu Lys Thr Pro Ser Ala Ala Tyr Leu Trp Val Gly Thr
        595                 600                 605

Gly Ala Ser Glu Ala Glu Lys Thr Gly Ala Gln Glu Leu Leu Arg Val
```

```
                610             615             620
Leu Arg Ala Gln Pro Val Gln Val Ala Glu Gly Ser Glu Pro Asp Gly
625                 630                 635                 640

Phe Trp Glu Ala Leu Gly Gly Lys Ala Ala Tyr Arg Thr Ser Pro Arg
                645                 650                 655

Leu Lys Asp Lys Lys Met Asp Ala His Pro Pro Arg Leu Phe Ala Cys
                660                 665                 670

Ser Asn Lys Ile Gly Arg Phe Val Ile Glu Glu Val Pro Gly Glu Leu
                675                 680                 685

Met Gln Glu Asp Leu Ala Thr Asp Val Met Leu Leu Asp Thr Trp
690                 695                 700

Asp Gln Val Phe Val Trp Val Gly Lys Asp Ser Gln Glu Glu Glu Lys
705                 710                 715                 720

Thr Glu Ala Leu Thr Ser Ala Lys Arg Tyr Ile Glu Thr Asp Pro Ala
                725                 730                 735

Asn Arg Asp Arg Arg Thr Pro Ile Thr Val Val Lys Gln Gly Phe Glu
                740                 745                 750

Pro Pro Ser Phe Val Gly Trp Phe Leu Gly Trp Asp Asp Asp Tyr Trp
                755                 760                 765

Ser Val Asp Pro Leu Asp Arg Ala Met Ala Glu Leu Ala Ala
770                 775                 780

<210> SEQ ID NO 4
<211> LENGTH: 396
<212> TYPE: PRT
<213> ORGANISM: Homo sapiens

<400> SEQUENCE: 4

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
                35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
                100                 105                 110

Leu Leu Pro His Ala Asn Glu Val Ser Gln Lys Ile Gly Asp Asn Leu
                115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
                180                 185                 190

Asn Val Glu Glu Leu Lys Gly Arg Leu Thr Pro Tyr Ala Asp Glu Phe
                195                 200                 205
```

-continued

Lys Val Lys Ile Asp Gln Thr Val Glu Glu Leu Arg Arg Ser Leu Ala
    210             215                 220

Pro Tyr Ala Gln Asp Thr Gln Glu Lys Leu Asn His Gln Leu Glu Gly
225             230                 235                 240

Leu Thr Phe Gln Met Lys Lys Asn Ala Glu Glu Leu Lys Ala Arg Ile
            245                 250                 255

Ser Ala Ser Ala Glu Glu Leu Arg Gln Arg Leu Ala Pro Leu Ala Glu
        260                 265                 270

Asp Val Arg Gly Asn Leu Arg Gly Asn Thr Glu Gly Leu Gln Lys Ser
            275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305             310                 315                 320

Gln Met Glu Gln Leu Arg Gln Lys Leu Gly Pro His Ala Gly Asp Val
            325                 330                 335

Glu Gly His Leu Ser Phe Leu Glu Lys Asp Leu Arg Asp Lys Val Asn
        340                 345                 350

Ser Phe Phe Ser Thr Phe Lys Glu Lys Glu Ser Gln Asp Lys Thr Leu
    355                 360                 365

Ser Leu Pro Glu Leu Glu Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 5
<211> LENGTH: 531
<212> TYPE: PRT
<213> ORGANISM: Homo sapiens

<400> SEQUENCE: 5

Met Ser Lys Pro His Ser Glu Ala Gly Thr Ala Phe Ile Gln Thr Gln
1               5                   10                  15

Gln Leu His Ala Ala Met Ala Asp Thr Phe Leu Glu His Met Cys Arg
            20                  25                  30

Leu Asp Ile Asp Ser Pro Pro Ile Thr Ala Arg Asn Thr Gly Ile Ile
        35                  40                  45

Cys Thr Ile Gly Pro Ala Ser Arg Ser Val Glu Thr Leu Lys Glu Met
    50                  55                  60

Ile Lys Ser Gly Met Asn Val Ala Arg Leu Asn Phe Ser His Gly Thr
65                  70                  75                  80

His Glu Tyr His Ala Glu Thr Ile Lys Asn Val Arg Thr Ala Thr Glu
                85                  90                  95

Ser Phe Ala Ser Asp Pro Ile Leu Tyr Arg Pro Val Ala Val Ala Leu
            100                 105                 110

Asp Thr Lys Gly Pro Glu Ile Arg Thr Gly Leu Ile Lys Gly Ser Gly
        115                 120                 125

Thr Ala Glu Val Glu Leu Lys Lys Gly Ala Thr Leu Lys Ile Thr Leu
    130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val
                165                 170                 175

Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
            195                 200                 205

Val Asn Leu Pro Gly Ala Ala Val Asp Leu Pro Ala Val Ser Glu Lys
            210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
            245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
            275                 280                 285

Gly Ile Met Val Ala Arg Gly Asp Leu Gly Ile Glu Ile Pro Ala Glu
            290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
            325                 330                 335

Lys Pro Arg Pro Thr Arg Ala Glu Gly Ser Asp Val Ala Asn Ala Val
            340                 345                 350

Leu Asp Gly Ala Asp Cys Ile Met Leu Ser Gly Glu Thr Ala Lys Gly
            355                 360                 365

Asp Tyr Pro Leu Glu Ala Val Arg Met Gln His Leu Ile Ala Arg Glu
            370                 375                 380

Ala Glu Ala Ala Ile Tyr His Leu Gln Leu Phe Glu Glu Leu Arg Arg
385                 390                 395                 400

Leu Ala Pro Ile Thr Ser Asp Pro Thr Glu Ala Thr Ala Val Gly Ala
            405                 410                 415

Val Glu Ala Ser Phe Lys Cys Cys Ser Gly Ala Ile Ile Val Leu Thr
            420                 425                 430

Lys Ser Gly Arg Ser Ala His Gln Val Ala Arg Tyr Arg Pro Arg Ala
            435                 440                 445

Pro Ile Ile Ala Val Thr Arg Asn Pro Gln Thr Ala Arg Gln Ala His
            450                 455                 460

Leu Tyr Arg Gly Ile Phe Pro Val Leu Cys Lys Asp Pro Val Gln Glu
465                 470                 475                 480

Ala Trp Ala Glu Asp Val Asp Leu Arg Val Asn Phe Ala Met Asn Val
            485                 490                 495

Gly Lys Ala Arg Gly Phe Phe Lys Lys Gly Asp Val Val Ile Val Leu
            500                 505                 510

Thr Gly Trp Arg Pro Gly Ser Gly Phe Thr Asn Thr Met Arg Val Val
            515                 520                 525

Pro Val Pro
    530

<210> SEQ ID NO 6
<211> LENGTH: 577
<212> TYPE: PRT
<213> ORGANISM: Homo sapiens

<400> SEQUENCE: 6

Met Pro Lys Thr Ile Ser Val Arg Val Thr Thr Met Asp Ala Glu Leu
1               5                   10                  15

Glu Phe Ala Ile Gln Pro Asn Thr Thr Gly Lys Gln Leu Phe Asp Gln

```
            20                  25                  30
Val Val Lys Thr Ile Gly Leu Arg Glu Val Trp Phe Phe Gly Leu Gln
            35                  40                  45
Tyr Gln Asp Thr Lys Gly Phe Ser Thr Trp Leu Lys Leu Asn Lys Lys
            50                  55                  60
Val Thr Ala Gln Asp Val Arg Lys Glu Ser Pro Leu Leu Phe Lys Phe
65                  70                  75                  80
Arg Ala Lys Phe Tyr Pro Glu Asp Val Ser Glu Glu Leu Ile Gln Asp
                85                  90                  95
Ile Thr Gln Arg Leu Phe Phe Leu Gln Val Lys Glu Gly Ile Leu Asn
            100                 105                 110
Asp Asp Ile Tyr Cys Pro Pro Glu Thr Ala Val Leu Leu Ala Ser Tyr
            115                 120                 125
Ala Val Gln Ser Lys Tyr Gly Asp Phe Asn Lys Glu Val His Lys Ser
            130                 135                 140
Gly Tyr Leu Ala Gly Asp Lys Leu Leu Pro Gln Arg Val Leu Glu Gln
145                 150                 155                 160
His Lys Leu Asn Lys Asp Gln Trp Glu Glu Arg Ile Gln Val Trp His
                165                 170                 175
Glu Glu His Arg Gly Met Leu Arg Glu Asp Ala Val Leu Glu Tyr Leu
            180                 185                 190
Lys Ile Ala Gln Asp Leu Glu Met Tyr Gly Val Asn Tyr Phe Ser Ile
            195                 200                 205
Lys Asn Lys Lys Gly Ser Glu Leu Trp Leu Gly Val Asp Ala Leu Gly
            210                 215                 220
Leu Asn Ile Tyr Glu Gln Asn Asp Arg Leu Thr Pro Lys Ile Gly Phe
225                 230                 235                 240
Pro Trp Ser Glu Ile Arg Asn Ile Ser Phe Asn Asp Lys Lys Phe Val
                245                 250                 255
Ile Lys Pro Ile Asp Lys Lys Ala Pro Asp Phe Val Phe Tyr Ala Pro
            260                 265                 270
Arg Leu Arg Ile Asn Lys Arg Ile Leu Ala Leu Cys Met Gly Asn His
            275                 280                 285
Glu Leu Tyr Met Arg Arg Arg Lys Pro Asp Thr Ile Glu Val Gln Gln
            290                 295                 300
Met Lys Ala Gln Ala Arg Glu Glu Lys His Gln Lys Gln Met Glu Arg
305                 310                 315                 320
Ala Met Leu Glu Asn Glu Lys Lys Arg Glu Met Ala Glu Lys Glu
                325                 330                 335
Lys Glu Lys Ile Glu Arg Glu Lys Glu Glu Leu Met Glu Arg Leu Lys
            340                 345                 350
Gln Ile Glu Glu Gln Thr Lys Lys Ala Gln Gln Glu Leu Glu Glu Gln
            355                 360                 365
Thr Arg Arg Ala Leu Glu Leu Glu Gln Glu Arg Lys Arg Ala Gln Ser
            370                 375                 380
Glu Ala Glu Lys Leu Ala Lys Glu Arg Gln Glu Ala Glu Glu Ala Lys
385                 390                 395                 400
Glu Ala Leu Leu Gln Ala Ser Arg Asp Gln Lys Lys Thr Gln Glu Gln
                405                 410                 415
Leu Ala Leu Glu Met Ala Glu Leu Thr Ala Arg Ile Ser Gln Leu Glu
            420                 425                 430
Met Ala Arg Gln Lys Lys Glu Ser Glu Ala Val Glu Trp Gln Gln Lys
            435                 440                 445
```

```
Ala Gln Met Val Gln Glu Asp Leu Glu Lys Thr Arg Ala Glu Leu Lys
    450                 455                 460

Thr Ala Met Ser Thr Pro His Val Ala Glu Pro Ala Glu Asn Glu Gln
465                 470                 475                 480

Asp Glu Gln Asp Glu Asn Gly Ala Glu Ala Ser Ala Asp Leu Arg Ala
                485                 490                 495

Asp Ala Met Ala Lys Asp Arg Ser Glu Glu Arg Thr Thr Glu Ala
                500                 505                 510

Glu Lys Asn Glu Arg Val Gln Lys His Leu Lys Ala Leu Thr Ser Glu
    515                 520                 525

Leu Ala Asn Ala Arg Asp Glu Ser Lys Lys Thr Ala Asn Asp Met Ile
530                 535                 540

His Ala Glu Asn Met Arg Leu Gly Arg Asp Lys Tyr Lys Thr Leu Arg
545                 550                 555                 560

Gln Ile Arg Gln Gly Asn Thr Lys Gln Arg Ile Asp Glu Phe Glu Ser
                565                 570                 575

Met

<210> SEQ ID NO 7
<211> LENGTH: 248
<212> TYPE: PRT
<213> ORGANISM: Homo sapiens

<400> SEQUENCE: 7

Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Gly Ala Val Glu Lys
            20                  25                  30

Gly Glu Glu Leu Ser Cys Glu Glu Arg Asn Leu Leu Ser Val Ala Tyr
        35                  40                  45

Lys Asn Val Val Gly Gly Gln Arg Ala Ala Trp Arg Val Leu Ser Ser
50                  55                  60

Ile Glu Gln Lys Ser Asn Glu Glu Gly Ser Glu Glu Lys Gly Pro Glu
65                  70                  75                  80

Val Arg Glu Tyr Arg Glu Lys Val Glu Thr Glu Leu Gln Gly Val Cys
                85                  90                  95

Asp Thr Val Leu Gly Leu Leu Asp Ser His Leu Ile Lys Glu Ala Gly
            100                 105                 110

Asp Ala Glu Ser Arg Val Phe Tyr Leu Lys Met Lys Gly Asp Tyr Tyr
        115                 120                 125

Arg Tyr Leu Ala Glu Val Ala Thr Gly Asp Asp Lys Lys Arg Ile Ile
130                 135                 140

Asp Ser Ala Arg Ser Ala Tyr Gln Glu Ala Met Asp Ile Ser Lys Lys
145                 150                 155                 160

Glu Met Pro Pro Thr Asn Pro Ile Arg Leu Gly Leu Ala Leu Asn Phe
                165                 170                 175

Ser Val Phe His Tyr Glu Ile Ala Asn Ser Pro Glu Glu Ala Ile Ser
            180                 185                 190

Leu Ala Lys Thr Thr Phe Asp Glu Ala Met Ala Asp Leu His Thr Leu
        195                 200                 205

Ser Glu Asp Ser Tyr Lys Asp Ser Thr Leu Ile Met Gln Leu Leu Arg
    210                 215                 220

Asp Asn Leu Thr Leu Trp Thr Ala Asp Asn Ala Gly Glu Glu Gly Gly
225                 230                 235                 240
```

Glu Ala Pro Gln Glu Pro Gln Ser
                245

<210> SEQ ID NO 8
<211> LENGTH: 543
<212> TYPE: PRT
<213> ORGANISM: Homo sapiens

<400> SEQUENCE: 8

Met Glu Gln Val Asn Glu Leu Lys Glu Lys Gly Asn Lys Ala Leu Ser
1               5                   10                  15

Val Gly Asn Ile Asp Asp Ala Leu Gln Cys Tyr Ser Glu Ala Ile Lys
            20                  25                  30

Leu Asp Pro His Asn His Val Leu Tyr Ser Asn Arg Ser Ala Ala Tyr
        35                  40                  45

Ala Lys Lys Gly Asp Tyr Gln Lys Ala Tyr Glu Asp Gly Cys Lys Thr
    50                  55                  60

Val Asp Leu Lys Pro Asp Trp Gly Lys Gly Tyr Ser Arg Lys Ala Ala
65                  70                  75                  80

Ala Leu Glu Phe Leu Asn Arg Phe Glu Glu Ala Lys Arg Thr Tyr Glu
                85                  90                  95

Glu Gly Leu Lys His Glu Ala Asn Asn Pro Gln Leu Lys Glu Gly Leu
            100                 105                 110

Gln Asn Met Glu Ala Arg Leu Ala Glu Arg Lys Phe Met Asn Pro Phe
        115                 120                 125

Asn Met Pro Asn Leu Tyr Gln Lys Leu Glu Ser Asp Pro Arg Thr Arg
130                 135                 140

Thr Leu Leu Ser Asp Pro Thr Tyr Arg Glu Leu Ile Glu Gln Leu Arg
145                 150                 155                 160

Asn Lys Pro Ser Asp Leu Gly Thr Lys Leu Gln Asp Pro Arg Ile Met
                165                 170                 175

Thr Thr Leu Ser Val Leu Leu Gly Val Asp Leu Gly Ser Met Asp Glu
            180                 185                 190

Glu Glu Glu Ile Ala Thr Pro Pro Pro Pro Pro Lys Lys Glu
        195                 200                 205

Thr Lys Pro Glu Pro Met Glu Glu Asp Leu Pro Glu Asn Lys Lys Gln
    210                 215                 220

Ala Leu Lys Glu Lys Glu Leu Gly Asn Asp Ala Tyr Lys Lys Lys Asp
225                 230                 235                 240

Phe Asp Thr Ala Leu Lys His Tyr Asp Lys Ala Lys Glu Leu Asp Pro
                245                 250                 255

Thr Asn Met Thr Tyr Ile Thr Asn Gln Ala Ala Val Tyr Phe Glu Lys
            260                 265                 270

Gly Asp Tyr Asn Lys Cys Arg Glu Leu Cys Glu Lys Ala Ile Glu Val
        275                 280                 285

Gly Arg Glu Asn Arg Glu Asp Tyr Arg Gln Ile Ala Lys Ala Tyr Ala
    290                 295                 300

Arg Ile Gly Asn Ser Tyr Phe Lys Glu Lys Tyr Lys Asp Ala Ile
305                 310                 315                 320

His Phe Tyr Asn Lys Ser Leu Ala Glu His Arg Thr Pro Asp Val Leu
                325                 330                 335

Lys Lys Cys Gln Gln Ala Glu Lys Ile Leu Lys Glu Gln Glu Arg Leu
            340                 345                 350

Ala Tyr Ile Asn Pro Asp Leu Ala Leu Glu Glu Lys Asn Lys Gly Asn

```
                355                 360                 365
Glu Cys Phe Gln Lys Gly Asp Tyr Pro Gln Ala Met Lys His Tyr Thr
370                 375                 380
Glu Ala Ile Lys Arg Asn Pro Lys Asp Ala Lys Leu Tyr Ser Asn Arg
385                 390                 395                 400
Ala Ala Cys Tyr Thr Lys Leu Leu Glu Phe Gln Leu Ala Leu Lys Asp
                405                 410                 415
Cys Glu Glu Cys Ile Gln Leu Glu Pro Thr Phe Ile Lys Gly Tyr Thr
            420                 425                 430
Arg Lys Ala Ala Ala Leu Glu Ala Met Lys Asp Tyr Thr Lys Ala Met
435                 440                 445
Asp Val Tyr Gln Lys Ala Leu Asp Leu Asp Ser Ser Cys Lys Glu Ala
        450                 455                 460
Ala Asp Gly Tyr Gln Arg Cys Met Met Ala Gln Tyr Asn Arg His Asp
465                 470                 475                 480
Ser Pro Glu Asp Val Lys Arg Arg Ala Met Ala Asp Pro Glu Val Gln
                485                 490                 495
Gln Ile Met Ser Asp Pro Ala Met Arg Leu Ile Leu Glu Gln Met Gln
            500                 505                 510
Lys Asp Pro Gln Ala Leu Ser Glu His Leu Lys Asn Pro Val Ile Ala
515                 520                 525
Gln Lys Ile Gln Lys Leu Met Asp Val Gly Leu Ile Ala Ile Arg
        530                 535                 540

<210> SEQ ID NO 9
<211> LENGTH: 418
<212> TYPE: PRT
<213> ORGANISM: Homo sapiens

<400> SEQUENCE: 9

Met Arg Ser Leu Leu Leu Ser Ala Phe Cys Leu Leu Glu Ala Ala
1               5                   10                  15
Leu Ala Ala Glu Val Lys Lys Pro Ala Ala Ala Ala Pro Gly Thr
            20                  25                  30
Ala Glu Lys Leu Ser Pro Lys Ala Ala Thr Leu Ala Glu Arg Ser Ala
        35                  40                  45
Gly Leu Ala Phe Ser Leu Tyr Gln Ala Met Ala Lys Asp Gln Ala Val
    50                  55                  60
Glu Asn Ile Leu Val Ser Pro Val Val Ala Ser Ser Leu Gly Leu
65                  70                  75                  80
Val Ser Leu Gly Gly Lys Ala Thr Thr Ala Ser Gln Ala Lys Ala Val
                85                  90                  95
Leu Ser Ala Glu Gln Leu Arg Asp Glu Val His Ala Gly Leu Gly
            100                 105                 110
Glu Leu Leu Arg Ser Leu Ser Asn Ser Thr Ala Arg Asn Val Thr Trp
        115                 120                 125
Lys Leu Gly Ser Arg Leu Tyr Gly Pro Ser Ser Val Ser Phe Ala Asp
    130                 135                 140
Asp Phe Val Arg Ser Ser Lys Gln His Tyr Asn Cys Glu His Ser Lys
145                 150                 155                 160
Ile Asn Phe Arg Asp Lys Arg Ser Ala Leu Gln Ser Ile Asn Glu Trp
                165                 170                 175
Ala Ala Gln Thr Thr Asp Gly Lys Leu Pro Glu Val Thr Lys Asp Val
            180                 185                 190
```

-continued

Glu Arg Thr Asp Gly Ala Leu Leu Val Asn Ala Met Phe Lys Pro
        195                 200                 205

His Trp Asp Glu Lys Phe His His Lys Met Val Asp Asn Arg Gly Phe
210                 215                 220

Met Val Thr Arg Ser Tyr Thr Val Gly Val Met Met His Arg Thr
225                 230                 235                 240

Gly Leu Tyr Asn Tyr Tyr Asp Asp Glu Lys Glu Lys Leu Gln Ile Val
                245                 250                 255

Glu Met Pro Leu Ala His Lys Leu Ser Ser Leu Ile Ile Leu Met Pro
            260                 265                 270

His His Val Glu Pro Leu Glu Arg Leu Glu Lys Leu Leu Thr Lys Glu
            275                 280                 285

Gln Leu Lys Ile Trp Met Gly Lys Met Gln Lys Lys Ala Val Ala Ile
290                 295                 300

Ser Leu Pro Lys Gly Val Val Glu Val Thr His Asp Leu Gln Lys His
305                 310                 315                 320

Leu Ala Gly Leu Gly Leu Thr Glu Ala Ile Asp Lys Asn Lys Ala Asp
                325                 330                 335

Leu Ser Arg Met Ser Gly Lys Lys Asp Leu Tyr Leu Ala Ser Val Phe
                340                 345                 350

His Ala Thr Ala Phe Glu Leu Asp Thr Asp Gly Asn Pro Phe Asp Gln
            355                 360                 365

Asp Ile Tyr Gly Arg Glu Glu Leu Arg Ser Pro Lys Leu Phe Tyr Ala
            370                 375                 380

Asp His Pro Phe Ile Phe Leu Val Arg Asp Thr Gln Ser Gly Ser Leu
385                 390                 395                 400

Leu Phe Ile Gly Arg Leu Val Arg Pro Lys Gly Asp Lys Met Arg Asp
                405                 410                 415

Glu Leu

<210> SEQ ID NO 10
<211> LENGTH: 289
<212> TYPE: PRT
<213> ORGANISM: Homo sapiens

<400> SEQUENCE: 10

Met Ser Gly Phe Ser Thr Glu Glu Arg Ala Pro Phe Ser Leu Glu
1               5                   10                  15

Tyr Arg Val Phe Leu Lys Asn Glu Lys Gly Gln Tyr Ile Ser Pro Phe
                20                  25                  30

His Asp Ile Pro Ile Tyr Ala Asp Lys Asp Val Phe His Met Val Val
            35                  40                  45

Glu Val Pro Arg Trp Ser Asn Ala Lys Met Glu Ile Ala Thr Lys Asp
50                  55                  60

Pro Leu Asn Pro Ile Lys Gln Asp Val Lys Lys Gly Lys Leu Arg Tyr
65                  70                  75                  80

Val Ala Asn Leu Phe Pro Tyr Lys Gly Tyr Ile Trp Asn Tyr Gly Ala
                85                  90                  95

Ile Pro Gln Thr Trp Glu Asp Pro Gly His Asn Asp Lys His Thr Gly
            100                 105                 110

Cys Cys Gly Asp Asn Asp Pro Ile Asp Val Cys Glu Ile Gly Ser Lys
            115                 120                 125

Val Cys Ala Arg Gly Glu Ile Ile Gly Val Lys Val Leu Gly Ile Leu
130                 135                 140

```
Ala Met Ile Asp Glu Gly Glu Thr Asp Trp Lys Val Ile Ala Ile Asn
145                 150                 155                 160

Val Asp Asp Pro Asp Ala Ala Asn Tyr Asn Asp Ile Asn Asp Val Lys
            165                 170                 175

Arg Leu Lys Pro Gly Tyr Leu Glu Ala Thr Val Asp Trp Phe Arg Arg
            180                 185                 190

Tyr Lys Val Pro Asp Gly Lys Pro Glu Asn Glu Phe Ala Phe Asn Ala
            195                 200                 205

Glu Phe Lys Asp Lys Asp Phe Ala Ile Asp Ile Lys Ser Thr His
            210                 215                 220

Asp His Trp Lys Ala Leu Val Thr Lys Thr Asn Gly Lys Gly Ile
225                 230                 235                 240

Ser Cys Met Asn Thr Thr Leu Ser Glu Ser Pro Phe Lys Cys Asp Pro
            245                 250                 255

Asp Ala Ala Arg Ala Ile Val Asp Ala Leu Pro Pro Cys Glu Ser
            260                 265                 270

Ala Cys Thr Val Pro Thr Asp Val Asp Lys Trp Phe His His Gln Lys
            275                 280                 285

Asn

<210> SEQ ID NO 11
<211> LENGTH: 127
<212> TYPE: PRT
<213> ORGANISM: Homo sapiens

<400> SEQUENCE: 11

Met Ser Phe Ser Gly Lys Tyr Gln Leu Gln Ser Gln Glu Asn Phe Glu
1               5                   10                  15

Ala Phe Met Lys Ala Ile Gly Leu Pro Glu Glu Leu Ile Gln Lys Gly
            20                  25                  30

Lys Asp Ile Lys Gly Val Ser Glu Ile Val Gln Asn Gly Lys His Phe
            35                  40                  45

Lys Phe Thr Ile Thr Ala Gly Ser Lys Val Ile Gln Asn Glu Phe Thr
        50                  55                  60

Val Gly Glu Glu Cys Glu Leu Glu Thr Met Thr Gly Glu Lys Val Lys
65                  70                  75                  80

Thr Val Val Gln Leu Glu Gly Asp Asn Lys Leu Val Thr Thr Phe Lys
                85                  90                  95

Asn Ile Lys Ser Val Thr Glu Leu Asn Gly Asp Ile Ile Thr Asn Thr
            100                 105                 110

Met Thr Leu Gly Asp Ile Val Phe Lys Arg Ile Ser Lys Arg Ile
            115                 120                 125

<210> SEQ ID NO 12
<211> LENGTH: 397
<212> TYPE: PRT
<213> ORGANISM: Homo sapiens

<400> SEQUENCE: 12

Met Ala Leu Leu Arg Gly Val Phe Val Val Ala Ala Lys Arg Thr Pro
1               5                   10                  15

Phe Gly Ala Tyr Gly Gly Leu Leu Lys Asp Phe Thr Ala Thr Asp Leu
            20                  25                  30

Ser Glu Phe Ala Ala Lys Ala Ala Leu Ser Ala Gly Lys Val Ser Pro
            35                  40                  45

Glu Thr Val Asp Ser Val Ile Met Gly Asn Val Leu Gln Ser Ser Ser
```

```
                 50                   55                  60
Asp Ala Ile Tyr Leu Ala Arg His Val Gly Leu Arg Val Gly Ile Pro
 65                  70                  75                  80

Lys Glu Thr Pro Ala Leu Thr Ile Asn Arg Leu Cys Gly Ser Gly Phe
                 85                  90                  95

Gln Ser Ile Val Asn Gly Cys Gln Glu Ile Cys Val Lys Glu Ala Glu
                100                 105                 110

Val Val Leu Cys Gly Gly Thr Glu Ser Met Ser Gln Ala Pro Tyr Cys
            115                 120                 125

Val Arg Asn Val Arg Phe Gly Thr Lys Leu Gly Ser Asp Ile Lys Leu
            130                 135                 140

Glu Asp Ser Leu Trp Val Ser Leu Thr Asp Gln His Val Gln Leu Pro
145                 150                 155                 160

Met Ala Met Thr Ala Glu Asn Leu Ala Val Lys His Lys Ile Ser Arg
                165                 170                 175

Glu Glu Cys Asp Lys Tyr Ala Leu Gln Ser Gln Gln Arg Trp Lys Ala
            180                 185                 190

Ala Asn Asp Ala Gly Tyr Phe Asn Asp Glu Met Ala Pro Ile Glu Val
            195                 200                 205

Lys Thr Lys Lys Gly Lys Gln Thr Met Gln Val Asp Glu His Ala Arg
210                 215                 220

Pro Gln Thr Thr Leu Glu Gln Leu Gln Lys Leu Pro Pro Val Phe Lys
225                 230                 235                 240

Lys Asp Gly Thr Val Thr Ala Gly Asn Ala Ser Gly Val Ala Asp Gly
                245                 250                 255

Ala Gly Ala Val Ile Ile Ala Ser Glu Asp Ala Val Lys Lys His Asn
            260                 265                 270

Phe Thr Pro Leu Ala Arg Ile Val Gly Tyr Phe Val Ser Gly Cys Asp
            275                 280                 285

Pro Ser Ile Met Gly Ile Gly Pro Val Pro Ala Ile Ser Gly Ala Leu
            290                 295                 300

Lys Lys Ala Gly Leu Ser Leu Lys Asp Met Asp Leu Val Glu Val Asn
305                 310                 315                 320

Glu Ala Phe Ala Pro Gln Tyr Leu Ala Val Glu Arg Ser Leu Asp Leu
                325                 330                 335

Asp Ile Ser Lys Thr Asn Val Asn Gly Gly Ala Ile Ala Leu Gly His
                340                 345                 350

Pro Leu Gly Gly Ser Gly Ser Arg Ile Thr Ala His Leu Val His Glu
            355                 360                 365

Leu Arg Arg Arg Gly Gly Lys Tyr Ala Val Gly Ser Ala Cys Ile Gly
            370                 375                 380

Gly Gly Gln Gly Ile Ala Val Ile Ile Gln Ser Thr Ala
385                 390                 395

<210> SEQ ID NO 13
<211> LENGTH: 508
<212> TYPE: PRT
<213> ORGANISM: Homo sapiens

<400> SEQUENCE: 13

Met Gln Arg Leu Leu Thr Pro Val Lys Arg Ile Leu Gln Leu Thr Arg
 1               5                  10                  15

Ala Val Gln Glu Thr Ser Leu Thr Pro Ala Arg Leu Leu Pro Val Ala
                20                  25                  30
```

-continued

His Gln Arg Phe Ser Thr Ala Ser Ala Val Pro Leu Ala Lys Thr Asp
         35                  40                  45

Thr Trp Pro Lys Asp Val Gly Ile Leu Ala Leu Glu Val Tyr Phe Pro
 50                  55                  60

Ala Gln Tyr Val Asp Gln Thr Asp Leu Glu Lys Tyr Asn Asn Val Glu
 65                  70                  75                  80

Ala Gly Lys Tyr Thr Val Gly Leu Gly Gln Thr Arg Met Gly Phe Cys
                 85                  90                  95

Ser Val Gln Glu Asp Ile Asn Ser Leu Cys Leu Thr Val Val Gln Arg
                100                 105                 110

Leu Met Glu Arg Ile Gln Leu Pro Trp Asp Ser Val Gly Arg Leu Glu
            115                 120                 125

Val Gly Thr Glu Thr Ile Ile Asp Lys Ser Lys Ala Val Lys Thr Val
        130                 135                 140

Leu Met Glu Leu Phe Gln Asp Ser Gly Asn Thr Asp Ile Glu Gly Ile
145                 150                 155                 160

Asp Thr Thr Asn Ala Cys Tyr Gly Gly Thr Ala Ser Leu Phe Asn Ala
                165                 170                 175

Ala Asn Trp Met Glu Ser Ser Trp Asp Gly Arg Tyr Ala Met Val
            180                 185                 190

Val Cys Gly Asp Ile Ala Val Tyr Pro Ser Gly Asn Ala Arg Pro Thr
        195                 200                 205

Gly Gly Ala Gly Ala Val Ala Met Leu Ile Gly Pro Lys Ala Pro Leu
    210                 215                 220

Ala Leu Glu Arg Gly Leu Arg Gly Thr His Met Glu Asn Val Tyr Asp
225                 230                 235                 240

Phe Tyr Lys Pro Asn Leu Ala Ser Glu Tyr Pro Ile Val Asp Gly Lys
                245                 250                 255

Leu Ser Ile Gln Cys Tyr Leu Arg Ala Leu Asp Arg Cys Tyr Thr Ser
            260                 265                 270

Tyr Arg Lys Lys Ile Gln Asn Gln Trp Lys Gln Ala Gly Ser Asp Arg
        275                 280                 285

Pro Phe Thr Leu Asp Asp Leu Gln Tyr Met Ile Phe His Thr Pro Phe
    290                 295                 300

Cys Lys Met Val Gln Lys Ser Leu Ala Arg Leu Met Phe Asn Asp Phe
305                 310                 315                 320

Leu Ser Ala Ser Ser Asp Thr Gln Thr Ser Leu Tyr Lys Gly Leu Glu
                325                 330                 335

Ala Phe Gly Gly Leu Lys Leu Glu Asp Thr Tyr Thr Asn Lys Asp Leu
            340                 345                 350

Asp Lys Ala Leu Leu Lys Ala Ser Gln Asp Met Phe Asp Lys Lys Thr
        355                 360                 365

Lys Ala Ser Leu Tyr Leu Ser Thr His Asn Gly Asn Met Tyr Thr Ser
    370                 375                 380

Ser Leu Tyr Gly Cys Leu Ala Ser Leu Leu Ser His His Ser Ala Gln
385                 390                 395                 400

Glu Leu Ala Gly Ser Arg Ile Gly Ala Phe Ser Tyr Gly Ser Gly Leu
                405                 410                 415

Ala Ala Ser Phe Phe Ser Phe Arg Val Ser Gln Asp Ala Ala Pro Gly
            420                 425                 430

Ser Pro Leu Asp Lys Leu Val Ser Ser Thr Ser Asp Leu Pro Lys Arg
        435                 440                 445

Leu Ala Ser Arg Lys Cys Val Ser Pro Glu Glu Phe Thr Glu Ile Met

```
                  450                 455                 460
Asn Gln Arg Glu Gln Phe Tyr His Lys Val Asn Phe Ser Pro Pro Gly
465                 470                 475                 480

Asp Thr Asn Ser Leu Phe Pro Gly Thr Trp Tyr Leu Glu Arg Val Asp
                485                 490                 495

Glu Gln His Arg Arg Lys Tyr Ala Arg Arg Pro Val
                500                 505
```

<210> SEQ ID NO 14
<211> LENGTH: 500
<212> TYPE: PRT
<213> ORGANISM: Homo sapiens

<400> SEQUENCE: 14

```
Met Ala Ser Met Leu Leu Ala Gln Arg Leu Ala Cys Ser Phe Gln His
1               5                   10                  15

Ser Tyr Arg Leu Leu Val Pro Gly Ser Arg His Ile Ser Gln Ala Ala
                20                  25                  30

Ala Lys Val Asp Val Glu Phe Asp Tyr Asp Gly Pro Leu Met Lys Thr
            35                  40                  45

Glu Val Pro Gly Pro Arg Ser Gln Glu Leu Met Lys Gln Leu Asn Ile
50                  55                  60

Ile Gln Asn Ala Glu Ala Val His Phe Phe Cys Asn Tyr Glu Glu Ser
65                  70                  75                  80

Arg Gly Asn Tyr Leu Val Asp Val Asp Gly Asn Arg Met Leu Asp Leu
                85                  90                  95

Tyr Ser Gln Ile Ser Ser Val Pro Ile Gly Tyr Ser His Pro Ala Leu
                100                 105                 110

Leu Lys Leu Ile Gln Gln Pro Gln Asn Ala Ser Met Phe Val Asn Arg
            115                 120                 125

Pro Ala Leu Gly Ile Leu Pro Pro Glu Asn Phe Val Glu Lys Leu Arg
130                 135                 140

Gln Ser Leu Leu Ser Val Ala Pro Lys Gly Met Ser Gln Leu Ile Thr
145                 150                 155                 160

Met Ala Cys Gly Ser Cys Ser Asn Glu Asn Ala Leu Lys Thr Ile Phe
                165                 170                 175

Met Trp Tyr Arg Ser Lys Glu Arg Gly Gln Arg Gly Phe Ser Gln Glu
                180                 185                 190

Glu Leu Glu Thr Cys Met Ile Asn Gln Ala Pro Gly Cys Pro Asp Tyr
            195                 200                 205

Ser Ile Leu Ser Phe Met Gly Ala Phe His Gly Arg Thr Met Gly Cys
210                 215                 220

Leu Ala Thr Thr His Ser Lys Ala Ile His Lys Ile Asp Ile Pro Ser
225                 230                 235                 240

Phe Asp Trp Pro Ile Ala Pro Phe Pro Arg Leu Lys Tyr Pro Leu Glu
                245                 250                 255

Glu Phe Val Lys Glu Asn Gln Gln Glu Glu Ala Arg Cys Leu Glu Glu
                260                 265                 270

Val Glu Asp Leu Ile Val Lys Tyr Arg Lys Lys Lys Lys Thr Val Ala
            275                 280                 285

Gly Ile Ile Val Glu Pro Ile Gln Ser Glu Gly Gly Asp Asn His Ala
290                 295                 300

Ser Asp Asp Phe Phe Arg Lys Leu Arg Asp Ile Ala Arg Lys His Gly
305                 310                 315                 320
```

```
Cys Ala Phe Leu Val Asp Glu Val Gln Thr Gly Gly Cys Thr Gly
                325                 330                 335

Lys Phe Trp Ala His Glu His Trp Gly Leu Asp Asp Pro Ala Asp Val
            340                 345                 350

Met Thr Phe Ser Lys Lys Met Met Thr Gly Gly Phe Phe His Lys Glu
                355                 360                 365

Glu Phe Arg Pro Asn Ala Pro Tyr Arg Ile Phe Asn Thr Trp Leu Gly
        370                 375                 380

Asp Pro Ser Lys Asn Leu Leu Ala Glu Val Ile Asn Ile Ile Lys
385                 390                 395                 400

Arg Glu Asp Leu Leu Asn Asn Ala Ala His Ala Gly Lys Ala Leu Leu
                405                 410                 415

Thr Gly Leu Leu Asp Leu Gln Ala Arg Tyr Pro Gln Phe Ile Ser Arg
            420                 425                 430

Val Arg Gly Arg Gly Thr Phe Cys Ser Phe Asp Thr Pro Asp Asp Ser
                435                 440                 445

Ile Arg Asn Lys Leu Ile Leu Ile Ala Arg Asn Lys Gly Val Val Leu
        450                 455                 460

Gly Gly Cys Gly Asp Lys Ser Ile Arg Phe Arg Pro Thr Leu Val Phe
465                 470                 475                 480

Arg Asp His His Ala His Leu Phe Leu Asn Ile Phe Ser Asp Ile Leu
                485                 490                 495

Ala Asp Phe Lys
            500

<210> SEQ ID NO 15
<211> LENGTH: 406
<212> TYPE: PRT
<213> ORGANISM: Homo sapiens

<400> SEQUENCE: 15

Met Pro Pro Val Gly Gly Lys Lys Ala Lys Lys Gly Ile Leu Glu Arg
1               5                   10                  15

Leu Asn Ala Gly Glu Ile Val Ile Gly Asp Gly Gly Phe Val Phe Ala
            20                  25                  30

Leu Glu Lys Arg Gly Tyr Val Lys Ala Gly Pro Trp Thr Pro Glu Ala
        35                  40                  45

Ala Val Glu His Pro Glu Ala Val Arg Gln Leu His Arg Glu Phe Leu
    50                  55                  60

Arg Ala Gly Ser Asn Val Met Gln Thr Phe Thr Phe Tyr Ala Ser Glu
65                  70                  75                  80

Asp Lys Leu Glu Asn Arg Gly Asn Tyr Val Leu Glu Lys Ile Ser Gly
                85                  90                  95

Gln Glu Val Asn Glu Ala Ala Cys Asp Ile Ala Arg Gln Val Ala Asp
            100                 105                 110

Glu Gly Asp Ala Leu Val Ala Gly Gly Val Ser Gln Thr Pro Ser Tyr
        115                 120                 125

Leu Ser Cys Lys Ser Glu Thr Glu Val Lys Lys Val Phe Leu Gln Gln
    130                 135                 140

Leu Glu Val Phe Met Lys Lys Asn Val Asp Phe Leu Ile Ala Glu Tyr
145                 150                 155                 160

Phe Glu His Val Glu Glu Ala Val Trp Ala Val Glu Thr Leu Ile Ala
                165                 170                 175

Ser Gly Lys Pro Val Ala Ala Thr Met Cys Ile Gly Pro Glu Gly Asp
            180                 185                 190
```

```
Leu His Gly Val Pro Pro Gly Glu Cys Ala Val Arg Leu Val Lys Ala
        195             200                 205

Gly Ala Ser Ile Ile Gly Val Asn Cys His Phe Asp Pro Thr Ile Ser
    210             215                 220

Leu Lys Thr Val Lys Leu Met Lys Glu Gly Leu Glu Ala Ala Arg Leu
225                 230                 235                 240

Lys Ala His Leu Met Ser Gln Pro Leu Ala Tyr His Thr Pro Asp Cys
                245                 250                 255

Asn Lys Gln Gly Phe Ile Asp Leu Pro Glu Phe Pro Phe Gly Leu Glu
            260                 265                 270

Pro Arg Val Ala Thr Arg Trp Asp Ile Gln Lys Tyr Ala Arg Glu Ala
        275                 280                 285

Tyr Asn Leu Gly Val Arg Tyr Ile Gly Gly Cys Cys Gly Phe Glu Pro
    290                 295                 300

Tyr His Ile Arg Ala Ile Ala Glu Glu Leu Ala Pro Glu Arg Gly Phe
305             310                 315                 320

Leu Pro Pro Ala Ser Glu Lys His Gly Ser Trp Gly Ser Gly Leu Asp
                325                 330                 335

Met His Thr Lys Pro Trp Val Arg Ala Arg Ala Arg Lys Glu Tyr Trp
            340                 345                 350

Glu Asn Leu Arg Ile Ala Ser Gly Arg Pro Tyr Asn Pro Ser Met Ser
            355                 360                 365

Lys Pro Asp Gly Trp Gly Val Thr Lys Gly Thr Ala Glu Leu Met Gln
        370                 375                 380

Gln Lys Glu Ala Thr Thr Glu Gln Gln Leu Lys Glu Leu Phe Glu Lys
385                 390                 395                 400

Gln Lys Phe Lys Ser Gln
                405
```

BIOMARKERS FOR CHOLANGIOCELLULAR CARCINOMA (CCC)

The invention relates to a method for identifying specific marker proteins (biomarkers) for cholangiocellular carcinoma (CCC), the biomarkers for CCC identified by the method and the use thereof, in particular for diagnosis, surveillance and treatment. The invention further relates to a diagnostic device comprising the biomarkers for CCC and a screening assay wherein these biomarkers for CCC are used to identify novel pharmaceutical compounds for treatment of CCC.

Cholangiocellular carcinoma (CCC) is a malignant neoplasm which arises from the cholangiocytes, the epithelial cells lining the bile ducts. The firm, white tumours consisting of a significant amount of fibrous stroma are classified as intrahepatic, extrahepatic or hilar according to their anatomic location. Most common are the Klatskin tumours, originating from the confluence of the right and left hepatic ducts[1]. Compared to other types of cancer CCC is a relatively rare disease, accounting for about 3% of all gastrointestinal malignancies[2]. However, its incidence is increasing and due to poor patients outcome it has overtaken hepatocellular carcinoma (HCC) as the main cause of death from a primary liver tumour[3]. Reasons for the high mortality rate (5-year survival, rate of about 5%)[4] are the difficult diagnosis and limited treatment options. At present, extensive surgical resection of the extrahepatic bile ducts and parts of the liver or liver transplantation remain the only potentially curative treatment options, although most patients are considered inoperable at the time of diagnosis[5].

Tumour markers for CCC used in clinics at present show low sensitivity and specificity and are therefore not able to differentiate between benign and malignant bile duct stenosis reliably[5, 6]. Carbohydrate antigen 19-9 (CA19-9), the most widely used tumour marker, for example, does not detect CCC in an early stage and is also elevated in pancreatic cancer, gastric cancer, primary biliary cirrhosis, cholangitis, cholestasis and in smokers. Furthermore it is useless in 7% of the population who are Lewis-antigen negative[7, 8]. On the other hand, carcinoembryonic antigen (CEA), though detectable in serum and even in bile, is increased in only 30% of CCC patients. The diagnosis of CCC therefore requires a multimodality approach involving laboratory, radiologic, endoscopic, and pathologic analysis[9] with the final confirmation being obtained by histologic or cytologic examination[2].

The need for better tumour markers which enable diagnosis of CCC both in body fluids as well as by immunohistochemistry is apparent. Several proteomic studies using different sample types and various techniques have therefore been performed. The analysis of CCC cell lines, for example, has led to the identification of potential diagnostic and also prognostic biomarker candidates[10-12]. In addition, cell lines have been used to discover proteins predictive of the response to chemotherapy[13]. Since results from cell culture experiments do not always reflect the actual conditions in the tumour, the use of patient samples can be advantageous. Some of the recent studies have focused on serum[14, 15], urine[16] or bile[17-19]. Nevertheless, the most appropriate source of tumour-specific signals is tumour tissue which, in the past, has been analysed by two-dimensional electrophoresis[20] as well as mass spectrometry-based proteomic approaches such as histology-directed MALDI-TOF-MS[21], SELDI-TOF-MS[22] or LC-MS/MS[23]. So far, however, none of the potential biomarkers were successfully implemented into clinical routine.

Recently, it was demonstrated that the application of two complementary techniques, two-dimensional differential in-gel electrophoresis (2D-DIGE) and mass spectrometry-based label-free LC-MS/MS, is an auspicious tactic for the discovery of novel biomarker candidates in HCC tissue[24].

Proceeding from the described prior art, the object therefore presents itself of providing markers and devices for the early recognition and diagnosis of CCC.

Surprisingly, novel and specific biomarkers for CCC can be identified by the method according to the invention.

The present invention relates to a method for identifying biomarkers for cholangiocellular carcinoma (CCC) comprising the steps
a) collecting tumorous tissue samples and non-tumorous tissue samples from at least 5 patients with CCC;
b) comparing the tumorous tissue samples with the non-tumorous tissue samples by 2D-DIGE and thereby identifying biomarker candidates for CCC showing different expression in tumorous tissue and non-tumorous tissue;
c) comparing the tumorous tissue samples with the non-tumorous tissue samples by label-free liquid chromatography-mass spectrometry (LC-MS) and thereby identifying biomarker candidates for CCC showing different expression in tumorous tissue and non-tumorous tissue;
d) comparing the expression data of biomarker candidates obtained by 2D-DIGE according to step b) with the expression data of biomarker candidates obtained by label-free LC-MS according to step c) and thereby identifying biomarkers for CCC showing different expression with 2D-DIGE according to step b) and showing different expression with label-free LC-MS according to step c).

The method according to the invention combines two complementary techniques which leads to the identification of highly specific biomarkers for CCC. In addition, tissue samples from the same person are compared in steps b) and c), tumorous and non-tumorous tissue, which also reduces false positive results. The differential expression data is preferably further processed by statistical analysis, for example by the methods described in the examples and in table 3.

In a further embodiment the method according to the invention further comprises the step of immunohistochemical analysis of the biomarkers for CCC from step d) by using tumorous tissue of at least one CCC-patient and comparing the expression of the respective biomarker candidate in the tumorous tissue with the expression in non-tumorous tissue of the same patient and selecting those biomarkers for CCC that display a sensitivity of 40% or more for the detection of CCC tumour cells in the case of proteins found to be up-regulated in tumorous tissue or the detection of hepatocytes in the case of down-regulated proteins. In a preferred embodiment for immunohistochemical analysis tissue samples from persons that are different from those of step a), is applied.

In another aspect the present invention relates to a biomarker for CCC identified by a method according to the invention. In a preferred embodiment the biomarker for CCC is selected from the group comprising chloride intracellular channel protein 1, Tax1-binding protein 3, gelsolin, apolipoprotein A-IV, pyruvat kinase isoenzymes M1/M2, moesin, 14-3-3 protein sigma, stress-induced phosphoprotein 1, serpin H1, inorganic pyrophosphatase, fatty acid-binding protein (liver), 3-ketoacyl-CoA thiolase (mitochondrial), hydroxymethylglutaryl-CoA synthase (mitochondrial), 4-aminobutyrate aminotransferase (mitochondrial) and betaine-homocysteine S-methyltransferase 1, partial sequences or homologues of theses proteins, nucleic acids encoding for chloride intracellular channel protein 1, Tax1-binding protein 3, gelsolin, apolipoprotein A-IV, pyruvat kinase isoenzymes M1/M2, moesin, 14-3-3 protein sigma, stress-induced phosphoprotein 1, serpin H1, inorganic pyrophosphatase, fatty acid-binding protein (liver), 3-ketoacyl-CoA thiolase (mitochondrial), hydroxymethylglutaryl-CoA synthase (mitochondrial), 4-aminobutyrate aminotransferase (mitochondrial) and betaine-homocysteine S-methyltransferase 1, partial sequences or homologous of the respective nucleic acids.

Another embodiment of the invention relates to the use of the biomarkers for CCC identified by the method according to the invention. In particular the invention relates to the use of one or more biomarkers for CCC selected from the group of proteins comprising chloride intracellular chloride intracellular channel protein 1, Tax1-binding protein 3, gelsolin, apolipoprotein A-IV, pyruvat kinase isoenzymes M1/M2, moesin, 14-3-3 protein sigma, stress-induced phosphoprotein 1, serpin H1, inorganic pyrophosphatase, fatty acid-binding protein (liver), 3-ketoacyl-CoA thiolase (mitochondrial), hydroxymethylglutaryl-CoA synthase (mitochondrial), 4-aminobutyrate aminotransferase (mitochondrial) and betaine-homocysteine S-methyltransferase 1, partial sequences or homologues of theses proteins, nucleic acids encoding for chloride intracellular channel protein 1, Tax1-binding protein 3, gelsolin, apolipoprotein A-IV, pyruvat kinase isoenzymes M1/M2, moesin, 14-3-3 protein sigma, stress-induced phosphoprotein 1, serpin H1, inorganic pyrophosphatase, fatty acid-binding protein (liver), 3-ketoacyl-CoA thiolase (mitochondrial), hydroxymethylglutaryl-CoA synthase (mitochondrial), 4-aminobutyrate aminotransferase (mitochondrial) and betaine-homocysteine S-methyltransferase 1, partial sequences or homologous of the respective nucleic acids for differential diagnosis of CCC, early recognition of CCC, diagnosis of CCC, prognosis of CCC, evaluation of progression of CCC, prediction of outcome of treatment of CCC, evaluation of treatment of CCC, surveillance of treatment of CCC, surveillance of after-treatment of CCC.

In another embodiment, the invention relates to the use for the ex vivo analysis of a biological sample of a person, for example the analysis of body fluids or tissue.

In another embodiment, the invention relates to the use for determination of metastasis originate from the bile ducts or hepatocytes or a different cell type, as indicator for collagen biosynthesis in connection with CCC or fibrotic changes in connection with CCC, alterations in energy and/or lipid metabolism and/or enhanced proliferation and/or oxidative stress in connection with CCC.

In another embodiment, the invention relates to the use wherein at least two different biomarkers for CCC selected from the group of proteins comprising chloride intracellular channel protein 1, Tax1-binding protein 3, gelsolin, apolipoprotein A-IV, pyruvat kinase isoenzymes M1/M2, moesin, 14-3-3 protein sigma, stress-induced phosphoprotein 1, serpin H1, inorganic pyrophosphatase, fatty acid-binding protein (liver), 3-ketoacyl-CoA thiolase (mitochondrial), hydroxymethylglutaryl-CoA synthase (mitochondrial), 4-aminobutyrate aminotransferase (mitochondrial) and betaine-homocysteine S-methyltransferase 1, partial sequences or homologues of theses proteins, nucleic acids encoding for chloride intracellular channel protein 1, Tax1-binding protein 3, gelsolin, apolipoprotein A-IV, pyruvat kinase isoenzymes M1/M2, moesin, 14-3-3 protein sigma, stress-induced phosphoprotein 1, serpin H1, inorganic pyrophosphatase, fatty acid-binding protein (liver), 3-ketoacyl-CoA thiolase (mitochondrial), hydroxymethylglutaryl-CoA synthase (mitochondrial), 4-aminobutyrate aminotransferase (mitochondrial) and betaine-homocysteine S-methyltransferase 1, partial sequences or homologues of the respective nucleic acids, are employed.

In another aspect, the present invention relates to a diagnostic device or diagnostic kit for the detection of CCC comprising one or more biomarkers for CCC selected from the group of proteins comprising chloride intracellular channel protein 1, Tax1-binding protein 3, gelsolin, apolipoprotein A-IV, pyruvat kinase isoenzymes M1/M2, moesin, 14-3-3 protein sigma, stress-induced phosphoprotein 1, serpin H1, inorganic pyrophosphatase, fatty acid-binding protein (liver), 3-ketoacyl-CoA thiolase (mitochondrial), hydroxymethylglutaryl-CoA synthase (mitochondrial), 4-aminobutyrate aminotransferase (mitochondrial) and betaine-homocysteine S-methyltransferase 1, partial sequences or homologues of theses proteins, nucleic acids encoding for chloride intracellular channel protein 1, Tax1-binding protein 3, gelsolin, apolipoprotein A-IV, pyruvat kinase isoenzymes M1/M2, moesin, 14-3-3 protein sigma, stress-induced phosphoprotein 1, serpin H1, inorganic pyrophosphatase, fatty acid-binding protein (liver), 3-ketoacyl-CoA thiolase (mitochondrial), hydroxymethylglutaryl-CoA synthase (mitochondrial), 4-aminobutyrate aminotransferase (mitochondrial) and betaine-homocysteine S-methyltransferase 1, partial sequences or homologous of the respective nucleic acids, means for detection and optionally further aids.

In another aspect, the present invention relates to a method for studying a biological sample for CCC comprising the steps,
  a) collecting a biological sample from a person,
  b) bringing the biological sample into contact with one or more biomarkers for CCC selected from the group of proteins comprising chloride intracellular channel protein 1, Tax1-binding protein 3, gelsolin, apolipoprotein A-IV, pyruvat kinase isoenzymes M1/M2, moesin, 14-3-3 protein sigma, stress-induced phosphoprotein 1, serpin H1, inorganic pyrophosphatase, fatty acid-binding protein (liver), 3-ketoacyl-CoA thiolase (mitochondrial), hydroxymethylglutaryl-CoA synthase (mitochondrial), 4-aminobutyrate aminotransferase (mitochondrial) and betaine-homocysteine S-methyltransferase 1, partial sequences or homologues of theses proteins, nucleic acids encoding for chloride intracellular channel protein 1, Tax1-binding protein 3, gelsolin, apolipoprotein A-IV, pyruvat kinase isoenzymes M1/M2, moesin, 14-3-3 protein sigma, stress-induced phosphoprotein 1, serpin H1, inorganic pyrophosphatase, fatty acid-binding protein (liver), 3-ketoacyl-CoA thiolase (mitochondrial), hydroxymethylglutaryl-CoA synthase (mitochondrial), 4-aminobutyrate aminotransferase (mitochondrial) and betaine-homocysteine S-methyltransferase 1, partial sequences or homologous of the respective nucleic acids,
  c) determining, if the respective biomarker for CCC is more or less expressed in the biological sample to be studied in comparison to a control sample.

In a particular embodiment of the method, the biological sample is a human sample.

In another particular embodiment of the method, the biological sample is blood serum, blood plasma, whole blood, urine, bile, a biopsy sample, in particular a liver biopsy sample.

In another aspect the present invention relates to a screening assay for the identification and validation of pharmaceutical compounds for CCC comprising one or more biomarkers for CCC as selected from the group of proteins comprising chloride intracellular channel protein 1, Tax1-binding protein 3, gelsolin, apolipoprotein A-IV, pyruvat kinase isoenzymes M1/M2, moesin, 14-3-3 protein sigma, stress-induced phosphoprotein 1, serpin H1, inorganic pyrophosphatase, fatty acid-binding protein (liver), 3-ketoacyl-CoA thiolase (mitochondrial), hydroxymethylglutaryl-CoA synthase (mitochondrial), 4-aminobutyrate aminotransferase (mitochondrial) and betaine-homocysteine S-methyltransferase 1, partial sequences or homologues of theses proteins, nucleic acids encoding for chloride intracellular channel protein 1, Tax1-binding protein 3, gelsolin, apolipoprotein A-IV, pyruvat kinase isoenzymes M1/M2, moesin, 14-3-3 protein sigma, stress-induced phosphoprotein 1, serpin H1, inorganic pyrophosphatase, fatty acid-binding protein (liver), 3-ketoacyl-CoA thiolase (mitochondrial), hydroxymethylglutaryl-CoA synthase (mitochondrial), 4-aminobutyrate aminotransferase (mitochondrial) and betaine-homocysteine S-methyltransferase 1, partial sequences or homologous of the respective nucleic acids, and means for obtaining and detecting a signal indicating the binding of the compound to be investigated to one or more of the biomarkers for CCC.

In another aspect, the invention relates to a method of screening pharmaceutical compounds for treatment of CCC comprising the steps,
 a) bringing a compound to be investigated into contact with one or more biomarkers for CCC,
 b) determining, if the compound to be investigated binds to the one or more biomarkers for CCC.

In another aspect, the invention relates to a target for gene therapy of CCC, wherein the target is selected from one of the nucleic acid sequences encoding for chloride intracellular channel protein 1, Tax1-binding protein 3, gelsolin, apolipoprotein A-IV, pyruvat kinase isoenzymes M1/M2, moesin, 14-3-3 protein sigma, stress-induced phosphoprotein 1, serpin H1, inorganic pyrophosphatase, fatty acid-binding protein (liver), 3-ketoacyl-CoA thiolase (mitochondrial), hydroxymethylglutaryl-CoA synthase (mitochondrial) and 4-aminobutyrate aminotransferase (mitochondrial), betaine-homocysteine S-methyltransferase 1, partial sequences or homologues of theses nucleic acid sequences.

The present invention relates to a quantitative proteomic study characterized in a combination of two different techniques, namely the well-established 2D-DIGE (two-dimensional difference in gel electrophoresis) and a label-free ion-intensity-based quantification via mass spectrometry and liquid chromatography to identify CCC specific biomarkers. This is the first time such a combined study was performed with regard to cholangiocellular carcinoma. By comparing the results of both studies high-confident biomarker candidates of CCC could be identified. Furthermore, the comparison demonstrates the complementarity of the gel- and LC-MS-based techniques. To verify the differential protein expressions detected in the proteomic studies underlying the present invention additional immunological validations of the identified specific biomarkers for CCC were performed.

In the context of this invention, the term CCC comprises any form of cholangiocellular carcinoma (CCC). The terms are for example defined in Pschyrembel, Klinisches Wörterbuch [Clinical Dictionary], 263th edition, 2012, Berlin).

"Biomarkers for CCC", "Specific biomarkers for CCC", "specific biomarkers" in the context of the invention are the proteins defined by SEQ ID No. 1 to 15 according to the sequence listing. Preferred biomarkers are the proteins listed in table 3. Specific biomarkers are also the respective isoforms, homologous and partial sequences of theses proteins. According to the invention also the nucleic acids e.g. RNA, DNA, cDNA encoding for the specific biomarkers are enclosed. Instead of the respective proteins or amino acids the respective nucleic acids encoding for these biomarkers could be used for early recognition, diagnosis, evaluation of disease progression, surveillance of treatment, or after treatment. In preferred embodiments of the invention the specific biomarker for CCC is a protein or peptide, e.g. one of the proteins SEQ ID No. 1-15, one of the proteins listed in Table 3, or a nucleic acid that encodes for one of those proteins.

An "Isoform" of the respective protein, the specific biomarker, is any of several different forms of the same protein. Different forms of a protein may be produced from related genes, or may arise from the same gene by alternative splicing. A large number of isoforms are caused by single-nucleotide-polymorphisms or SNPs, small genetic differences between alleles of the same gene. These occur at specific individual nucleotide positions within a gene. Isoforms comprise also proteins with the same or similar amino acid sequence but different post-translational modification, like glycosylation. A glycoform is an isoform of a protein that differs only with respect to the number or type of attached glycan. Glycoproteins often consist of a number of different glycoforms, with alterations in the attached saccharide or oligosaccharide.

A "Homologue" of the respective protein, the specific biomarker, is defined in terms of shared ancestry. Two segments of DNA can have shared ancestry because of either a specification event (orthologs) or a duplication event (paralogs). The term "percent homology" and "sequence similarity" are used interchangeably. High sequence similarity might occur because of convergent evolution or because of chance. Such sequences are similar and are also included in the term according to the invention. Sequence regions that are homologous are also called conserved. Enclosed are also partial homology where a fraction of the sequences compared (are presumed to) share descent, while the rest does not. Many algorithms exist to cluster protein sequences into sequence families, which are sets of mutually homologous sequences, see for example databases HOVERGEN, HOMOLENS, HOGENOM. According to the invention homologues should display at least 80% or 90% or 95% identity in amino acid sequence, preferably 96% or 97%, most preferably 98% or 99% with one of the amino acid sequences SEQ ID NO. 1 to 15 or one of the nucleic acids encoding them.

"Partial Sequences" according to the invention have for example at least 50% or 60%, preferably at least 70% or 80%, most preferred at least 90% or 95% of the length of one of the amino acid sequences SEQ ID NO. 1 to 15 or one of the nucleic acids encoding them.

The specific biomarkers for CCC may be identified as potential biomarkers during a proteome analysis of CCC in comparison to non-CCC tissue. For this purpose, liver biopsy samples were taken from patients having CCC.

The proteins were labelled using a pigment and subjected to a 2-D polyacrylamide gel electrophoresis using isoelectric focusing in the first dimension and SDS gel electrophoresis in the second dimension. The results were compared for CCC and non-CCC cells with the aid of software suitable for this purpose, to detect and quantify the spots which were amplified or decreased in the CCC sample in comparison to the non-CCC sample. The emission of the pigments, with which the proteins were labelled, was measured and analyzed.

"Difference gel electrophoresis" (DIGE) is a form of gel electrophoresis where different protein samples can be labelled with fluorescent dyes (for example Cy3, Cy5, Cy2) prior to two-dimensional electrophoresis. Then, the labelled protein samples are mixed and put in the same gel. After the gel electrophoresis, the gel is scanned with the excitation wavelength of each dye one after the other, so each sample is analyzed separately. This technique is used to see changes in protein abundance. It overcomes limitations in traditional 2D electrophoresis that are due to inter-gel variation. This can be considerable even with identical samples. Since the proteins from the different sample types, e.g. healthy/diseased, virulent/non-virulent, are run on the same gel they can be directly compared. To do this with traditional 2D electrophoresis requires large numbers of time consuming repeats.

This study aiming at the identification of novel biomarker candidates for cholangiocellular carcinoma combined two quantitative proteomics techniques, 2D-DIGE and mass spectrometry-based label-free proteomics, to analyse the protein expression profile of CCC tumour tissue (n=8) in comparison to that of non-tumorous liver tissue (n=8). After an extensive evaluation of the resulting data promising biomarker candidates were verified by immunohistochemistry. The overall workflow is shown in FIG. 1.

Using the 2D-DIGE technique a total of 1676 protein spots were detected in at least 18 out of all 24 spot maps. Paired average ratios ranged from −30.54 to 30.19 and paired Student's T-tests down to $6.10e^{-8}$ were observed. Altogether, 808 spots were significantly differential between the two experimental groups (Student's T-test≤0.05; paired average ratio≥1.5). After the extraction from a preparative gel 219 protein spots, corresponding to 131 non-redundant proteins were identified by MALDI-TOF-MS. Among these, 50 proteins were up- and 81 were down-regulated in CCC tissue compared to controls. Three proteins—Triosephosphate isomerase, alpha-enolase and glutamate dehydrogenase 1—showed differing regulation directions between multiple detected isoforms (supplemental data).

Figure 2:
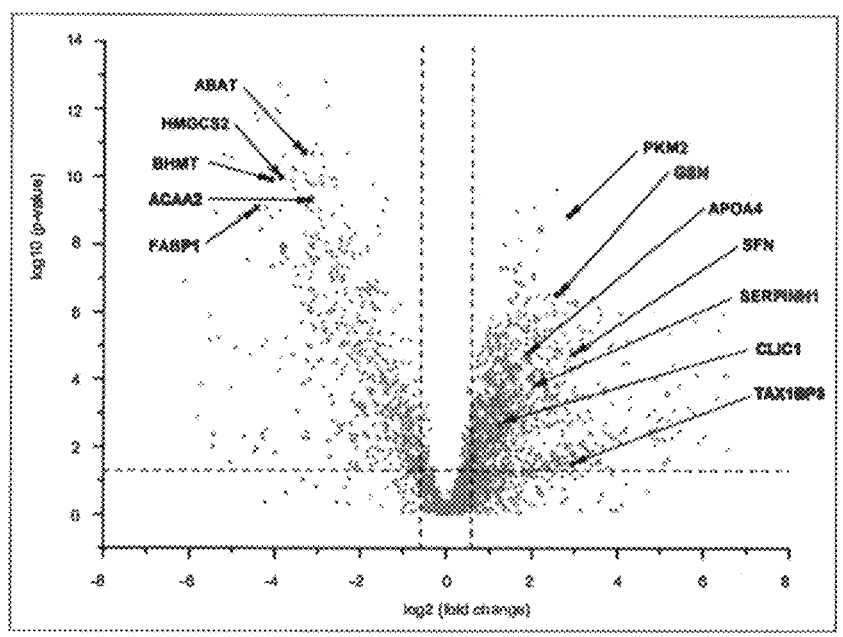

The same samples were also analysed by label-free LC-MS/MS. Due to technical issues the data of one control sample could not be evaluated. In the remaining 7 non-tumorous tissue samples and the 8 CCC tissue samples a total of 36,104 features charged positively 2-, 3- or 4-fold were detected. After the database search, 14,206 features were assigned to peptide matches leading to the identification of 2,404 proteins (FIG. 2). A significant regulation (p-value≤0.05; fold change≥1.5) was observed for 1,466 proteins with 924 being up- and 542 down-regulated in CCC tissue.

Figure 3:
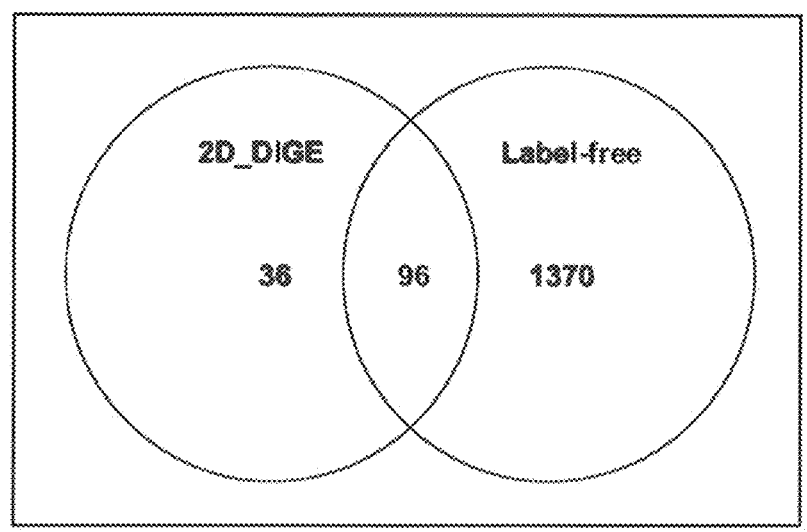

Comparing the protein lists from both approaches a total of 1,502 differential proteins were identified, while 36 were found exclusively in the 2D-DIGE experiment and 1,370 were identified only in the label-free study (FIG. 3). Hence, 96 proteins were found to be differential irrespective of the applied quantification method. This confirms the previously reported complementarity of both techniques[24].

Figure 4:
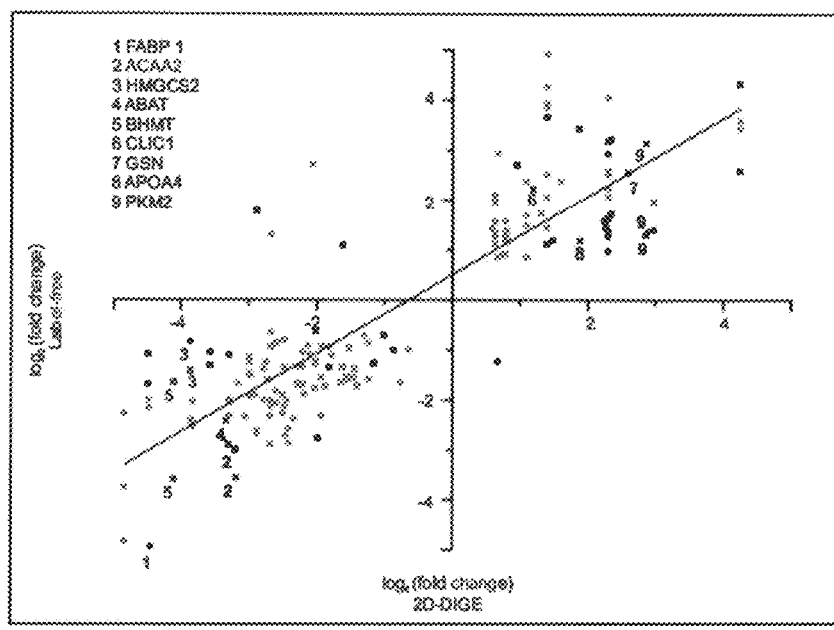

For most of the proteins from the overlap of both approaches the same regulation directions were discovered. A data analysis by means of linear regression shows a correlation of 75.6% of the fold changes determined by 2D-DIGE and label-free proteomics (Pearson R-value of 0.87) (FIG. 4). Nevertheless, five proteins (guanine deaminase, glutamate dehydrogenase 1, aminoacylase 1, 3-hydroxyisobutyryl-CoA hydrolase and Ig gamma-1 chain C region) were reported with contrary regulation directions in the 2D-DIGE and the label-free experiment. However, as mentioned previously, glutamate dehydrogenase 1 also showed inconsistent regulation directions of its four isoforms detected by 2D-DIGE.

Figure 5:
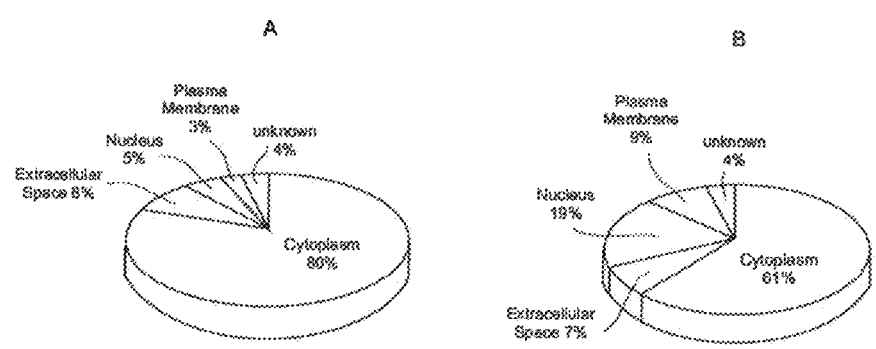

The determination of protein localisations using Ingenuity Pathway Analysis software revealed a significantly higher amount of nucleic and plasma membrane proteins which were identified by label-free proteomics compared to 2D-DIGE (FIG. 5). In the gel-based approach therefore a higher amount of cytoplasmic proteins was detected.

In order to select suitable candidates for the verification by immunohistochemistry a variety of different factors were taken into account. The Euclidian distance which, for the label-free experiment, is visualised by the volcano plot in (FIG. 2) was calculated using the fold change and the p-value of each protein[25]. Further, the confidence of the identification (mascot score and number of peptides) was observed. Intense manual as well as computer-aided literature research using SCAIView software (Fraunhofer Institute for Algorithms and Scientific Computing SCAI, Sankt Augustin, Germany)[26] gave additional hints which proteins might be appropriate candidates. This included evaluating which proteins have been described as being associated to CCC, other types of cancer or other liver diseases. Finally, the availability of appropriate antibodies also was an important factor. After these considerations 15 proteins which are summarized in table 3 were chosen for verification by immunohistochemistry.

An independent cohort of 14 patients was used for immunohistochemical verification of the 15 candidate proteins which showed good results in the proteomic analyses. Four of these proteins, namely tax1-binding protein 1 (Tax1BP3), gelsolin (GSN), stress-induced phosphoprotein 1 and 14-3-3 protein sigma (SFN), showed significantly stronger expression in CCC tissue compared to controls in all tested patients. This results in a sensitivity of 100%. None of these four proteins were detectable in hepatocytes; however GSN was immunoreactive in the tumour stroma as well as in sinusoidal cells of non-tumour liver tissue. The Tax1BP3 protein was also immunoreactive in the tumour stroma and in the bile duct epithelial cells of normal portal tracts. The 14-3-3 sigma protein was also detectable in non-neoplastic bile ducts. STIP1, however, was detectable exclusively in malignant CCC cells, not in the stroma, sinusoidal cells or normal hepatocytes and cholangiocytes.

Pyruvate kinase isozymes M1/M2 (PKM2), with a sensitivity of 86%, showed positive immunoreactivity in tumour cells as well as nuclei of stroma cells, but was negative in hepatocytes. Staining with antibodies against serpin H1 or chloride intracellular channel protein 1 (CLIC1) led to a calculated sensitivity of 64% for CCC tumour cells for both of these proteins. Serpin H1 was localised only to the cytoplasm of malignant cells while CLIC1 showed positive reactions in the entire tumour cells as well as in non-tumourous hepatic sinusoidal cells. Using an antibody against apolipoprotein A-IV (APOA4) an inhomogeneous regional staining of some hepatocytes and interstitial cells was observed. However, the signal in tumorous tissue was stronger in 57% of all samples. For inorganic pyrophosphatase (PPA1) a weak signal was visible in the control tissue, whereas tumorous cells were stained strongly. Connective tissue in the tumour was completely unstained. This expression pattern, however, was observed for only 43% of all samples. Fatty acid binding protein 1 (FABP1)

and Betaine-homocysteine S-methyltransferase 1 (BHMT) were shown to be down-regulated in CCC tissue as compared to non-tumorous liver tissue in the proteomics study. This result was confirmed by immunohistochemistry for all 14 patients. Hepatocytes displayed a strong positive signal for both these proteins while portal fields including cholangiocytes and connective tissue as well as tumorous tissue remained unstained. The remaining four candidates showed a tumour specificity of less than 40%.

The identification of novel biomarkers for the immunohistochemical diagnosis of CCC is an important task which was approached in this proteomic study. Tumorous and non-tumorous tissue samples were therefore compared by means of the top-down proteomic method 2D-DIGE as well as a bottom-up label-free LC-MS approach. Comparison and statistical evaluation of both lists of differentially regulated proteins led to the selection of 15 biomarker candidates of which 11 passed the verification by immunohistochemistry.

The advantages of combining 2D-DIGE and mass-spectrometry-based label-free proteomics for the discovery of novel biomarker candidates have been described previously and were confirmed once more by this study. The complementarity leading to higher proteome coverage increases the chance of identifying significant regulations. Regarding those proteins identified with both approaches, the correlation of these proteins fold changes from the two experiments ($R^2$=0.75) demonstrates the achieved accuracy. Only 5 out of 97 proteins showed differing regulation directions when comparing both techniques. For one of these, glutamate dehydrogenase 1, this can be explained by the different regulation directions of various isoforms detected in the 2D-DIGE experiment. This might also be the case for the other four proteins. With label-free proteomics it is not possible to distinguish between different isoforms of one protein so that the abundances are averaged.

For technical verification by immunohistochemistry 15 candidate proteins were chosen of which 11 showed sensitivities higher than 40%. These are Tax1BP3, gelsolin, STIP1, SFN, PKM2, serpin H1, CLIC1, APOA4, PPA1, FABP1 and BHMT and can be considered as potential biomarkers that might support the diagnosis of CCC.

Tax 1-binding protein 3 (Tax1BP3) is a small ubiquitously expressed protein that regulates a number of protein-protein interactions in a wide spectrum of biological processes such as cell development, polarization, proliferation and stress response[27-33]. It has been reported to be elevated in human invasive breast cancer cells where it contributes to cellular adhesion to extracellular matrix, invasion and pulmonary metastasis[34]. Furthermore, it is thought be a prognostic biomarker of human glioblastoma[35] and shows an inhibitory function in proliferation of colorectal cancer cells[28]. In this study, an increased expression level of Tax1BP3 in CCC tissue has been detected. The immunohistochemical verification however revealed its localisation in tumour cells as well as in non-tumorous cholangiocytes. This protein is therefore not a specific biomarker for CCC cells, but also detects normal bile duct cells. Therefore, TAX1BP3 is a potential marker which might be used to determine if metastasis originate from the bile ducts or a different cell type. Another possible application which will be evaluated in future experiments is the use of Tax1BP3 as a serum marker for CCC. We have demonstrated here that the overall abundance of this protein in tumorous CCC tissue is higher than in non-tumorous liver tissue although it is also expressed in normal cholangiocytes. This is due to the higher abundance of tumour cells compared to non-tumorous cells. If Tax1BP3 is secreted from the cells, it is likely to be elevated in patients' blood or perhaps other body fluids such as bile or urine when suffering from CCC.

The actin-modulating protein gelsolin was here found to be elevated in tumorous bile duct cells in comparison to hepatocytes and non-tumorous cholangiocytes. Due to the down-regulation in many other malignancies such as human breast, colorectal, gastric, bladder, lung, prostate, kidney, ovarian, pancreatic or oral cancers it has been assumed to act as a tumour suppressor. On the other hand, gelsolin overexpression has been associated to tumour recurrence and progression in urothelial tumours[36] as well as colorectal tumour cell invasion[37]. Considering the expression profile of gelsolin shown in this study it is a promising biomarker candidate for the histologic diagnosis of CCC.

14-3-3 protein sigma (SFN) which is involved in a large spectrum of signalling pathways is thought to be an important cell cycle protein in various cancer types[38-41]. In 2007, an immunohistochemical study demonstrated its expression in 67.7% of 93 tested cases of intrahepatic CCC. Immunoreactivity was observed only in cancerous tissue, not in normal bile duct cells[42]. This is in line with our findings. Furthermore, Kuroda et al.[42] demonstrated that decreased SFN expression is a significant indicator of poor prognosis in intrahepatic CCC. In conclusion, this protein might be used as a prognostic biomarker for CCC, and due to its connection to oncogenic processes in different malignancies it is a potential drug target.

A second candidate for a potential drug target might be pyruvate kinase isozymes M1/M2 (PKM2). This glycolytic enzyme catalyses the dephosphorylation of phosphoenolpyruvate (PEP) to pyruvate, thereby generating ATP. There are four isoforms of pyruvate kinase. The L type which is the major isozyme in the liver[43-45], the R type found in erythrocytes[46] and the M1 and M2 forms which are splice variants of the PKM gene product. Type M1 pyruvate kinase has the highest affinity to PEP and is therefore characteristic of tissues depending on rapid supply with high amounts of energy, such as muscle and brain[47-49]. The isozyme type M2, on the other hand, is expressed especially in proliferating cells, such as embryonic cells, adult stem cells and most cancer cells[48-51]. This means that during embryogenesis the M2 isoform is progressively replaced by the respective tissue specific isozyme, while the opposite takes place during carcinogenesis[45, 49, 50, 52, 53]. This suggests that PKM2 might also act as a prognostic tumour marker. Due to our findings of a PKM2 overexpression in CCC cells and results from previously published studies it is summarized that PKM2 might not be specific enough to distinguish CCC from other malignancies but it might be suitable for prognostic applications.

The label-free approach within our current study revealed an up-regulation of the collagen-binding protein serpin H1, also known as HSP47 or colligin. The increased expression was confirmed for 64% of all tested samples by immunohistochemical staining. Serpin H1 is thought to be involved in processing, glycosylation, and secretion of collagen and cross-linking the three dimensional assembly of type IV collagen molecules[54, 55]. Therefore, its overexpression in fibrotic diseases with enhanced collagen biosynthesis such as glomerulosclerosis[56], pulmonary fibrosis[57] and liver cirrhosis[58, 59] is not surprising. Other studies have also linked an increased serpin H1 expression to different types of cancer, for example, infiltrating ductal pancreatic adenocarcinoma[60], osteosarcoma[61] and ulcerative colitis-associated carcinomas[62]. In the present study, not only serpin H1 has been shown to be up-regulated in CCC tissue, but also seven types of collagen and various collagen-interacting proteins were overexpressed. This contributes to the dense fibrous texture of this tumour. In conclusion, increased expression of serpin H1 is an indicator for strong collagen biosynthesis and consequently for fibrotic changes in all kinds of tissue. Thus, it seems not to be specific for CCC but nevertheless might contribute to the overall applicability of a biomarker panel.

The redox-regulated protein chloride intracellular channel protein 1 (CLIC1) is involved in the regulation of the cell cycle as well as in the production of reactive oxygen species which act as second messengers in healthy cells, but also cause oxidative stress. In tumours which are characterised by both hyper-proliferation and oxidative stress overexpression of CLIC1 is not surprising[63]. Gel-based studies have demonstrated increased abundance of CLIC1 in gastric cancer[31] and in colorectal cancer[32] suggesting its use as novel biomarker. In hepatocellular carcinoma an up-regulation of this protein has been reported in proteomic[24, 64] as well as transcriptomic studies[65]. For CCC an overexpression of CLIC1 has been demonstrated for the first time in our current study. We were able to verify that immunohistochemical staining of this protein is suitable to differentiate between CCC tumour cells and non-tumorous liver tissue. Although in the verification a sensitivity of only 64% was reached it is worth taking this candidate to further validation studies in larger patient cohorts. This is especially because as a transient membrane protein CLIC1 might be a unique functional drug target during the tumorigenic process[63].

Apolipoprotein A-IV (APOA4) is a 376-amino acid glycoprotein which is suggested to be involved in chylomicron assembly and may act as a molecular chaperon escorting nascent pre-VLDL (very low-density lipoprotein) particles through the ER-Golgi secretory compartment[37]. Biosynthesis of APOA4 takes place mainly in intestinal enterocytes which secrete the apolipoprotein as a component of chylomicrons. In healthy human plasma APOA4 concentrations of ≈15 mg/dL are typical[66]. In different types of malignancies, such as pancreatic carcinoma[38], kidney cancer and ovarian cancer, however decreased concentrations in patients blood have been reported[39]. In the experiments presented here, tissue samples were examined which showed a significant overexpression of APOA4 in CCC cells compared to normal hepatocytes. Since, in this case, the sensitivity reached only 57% this might not be the most suitable candidate for a histologic marker. In body fluids however APOA4 might prove to be a promising biomarker which can therefore be used for non-invasive diagnosis.

Using the 2D-DIGE approach inorganic pyrophosphatase (PPA1) was identified as significantly up-regulated in CCC tissue. PPA1 is a ubiquitously expressed protein which catalyses the hydrolysis of pyrophosphate to orthophosphate. Pyrophosphate is formed as a by-product in many reactions that consume ATP or when nucleoside triphosphates are incorporated into DNA or RNA. Maintaining strict control over the intracellular pyrophosphate concentration is an essential process for the cell[67]. An overexpression of PPA1 has been described for ovarian cancer[40] as well as colorectal cancer[41], prostate cancer[68] and hepatocellular carcinoma[24]. Furthermore, cell migration, invasion and poor prognosis in gastric cancer seem to be associated with an up-regulation of PPA1[69]. The immunohistochemical analysis performed in our study verified PPA1 overexpression for 43% of the tested CCC tumour samples. Because, however, in these samples strong staining was restricted to the tumorous cells and there was hardly any signal detectable in non-tumorous hepatocytes, cholangiocytes or connective tissue.

One protein that showed higher expression levels in normal liver tissue than in CCC tumours is fatty acid-binding protein 1 (FABP1), also named L-type or liver-type fatty acid-binding protein (L-FABP). FABPs are small cytoplasmic proteins that bind free fatty acids and their coenzyme A derivatives as well as bilirubin and some other small molecules in the cytoplasm. They are expressed in tissues with an active fatty acid metabolism where they facilitate the intracellular transport of long-chain fatty acids[43], FABP1 is expressed mainly in hepatocytes[70], but also in the small intestines[71-73] and the kidney[74]. When cell damage occurs it is easily released into the circulation due to its small size and has therefore been reported to act as an early predictor of kidney injury detectable in urine[75]. In liver transplant recipients, FAPB1 plasma concentration rises significantly during hepatocyte injury due to rejection. Here, it can be detected earlier and with higher sensitivity than other biochemical plasma markers for acute liver injury such as alanine aminotransferase or alpha glutathione S-transferase[70]. Consistently with the literature, the immunohistochemical analysis performed in our study revealed the localisation of FABP1 in hepatocytes whereas tumorous and non-tumorous cholangiocytes remained completely unstained. Since FABP1 is generally detectable in body fluids, it might also be possible to identify alterations in FABP1 concentration in blood or urine from CCC patients. In addition, FABP1 might be used to differentiate metastasis deriving from hepatocytes from those of other origin.

Similar applications may be considered for betaine-homocysteine S-methyltransferase (BHMT) which regenerates methionine from homocysteine by remethylation in the kidney and the liver[76]. In the latter it accounts for 0.6-1.6% of total protein content[77]. This is in line with the strong expression discovered in hepatocytes in the study presented here. Decreased expression levels have been reported in hepatocellular carcinoma compared to normal liver tissue in several studies[78 79 80 24]. Nevertheless, the immunohistochemical staining of HCC tissue still showed a weak signal for BHMT[24] whereas CCC displayed none at all. This might additionally enable the use of this protein to distinguish between HCC and CCC.

In malignant cells a wide range of metabolic pathways are dysregulated. The overexpressed proteins identified and verified in this study display some of the cell functions which are altered in tumorous bile duct tissue. With GSN and serpin H1 we have identified markers for the fibrotic activity of the tumour cells which leads to the production of high amounts of extracellular matrix. Overexpression of PKM2, PPA1 and APOA4 points to alterations in energy and lipid metabolism, and the enhanced proliferation and oxidative stress tumour cells are generally characterized by was here confirmed by an up-regulation of SFN, Tax1BP3, PKM2 and CLIC1. The applicability of these proteins as biomarkers for CCC will be tested in future experiments. We suggest the consideration of GSN, SFN, serpin H1, CLIC1 and PPA1 as part of a biomarker panel to support pathologists with the histological diagnosis of CCC.

APOA4 is a promising candidate for a minimally invasive biomarker found in body fluids because it has previously been detected in serum, plasma and urine.

The following examples and figures are used to explain the invention without restricting the invention to the examples.

FIG. 1: Schematic presentation of the workflow followed in the proteomic study.

FIG. 2: Volcano Plot of all proteins identified in the label-free approach. Dashed lines indicate chosen cut-off values for the fold change (≥1.5) and the p-value (≤0.05). Proteins which were chosen for verification by immunohistochemistry are marked by arrows.

FIG. 3: Venn diagram showing the numbers of differential proteins identified exclusively by 2D-DIGE, by label-free proteomics or by both methods. Filter criteria were set to fold change>1.5 and p-value<0.05.

FIG. 4: Scatter plot visualising the correlation between the fold changes obtained from the gel-based and the label-free approach. Multiple datapoints corresponding to the same protein represent different isoforms detected in the 2D-DIGE experiment. The coefficient of determination $R^2$ is 0.758.

FIG. 5: Localisations of differential proteins identified by 2D-DIGE (A) and label-free proteomics (B).

EXAMPLES

Example 1: Clinical Data

Non-tumorous liver tissue and cholangiocellular carcinoma tissue from 21 CCC patients (14 females and 7 males) were collected during surgery at the University Hospital of Essen, Department of General, Visceral and Transplantation Surgery, Germany. The age of the patients ranged from 33 to 79 years (mean 62). Informed consent was obtained from each patient and the study protocol conforms to the ethical guidelines of the 1975 Declaration of Helsinki.

TABLE 1

Patient details and application of corresponding tissue samples in proteomic and verification experiments.

| Patient information | | | Sample used for | | |
| --- | --- | --- | --- | --- | --- |
| ID | Gender | Age | 2D-DIGE | label-free | IHC |
| 1 | Male | 74 | X | X | |
| 2 | Female | 59 | X | X | |
| 3 | Female | 61 | X | X | |
| 4 | Male | 42 | X | X | |
| 5 | Female | 46 | X | X | |
| 6 | Female | 62 | X | X | |
| 7 | Female | 78 | X | X | |
| 8 | Female | 70 | X | X | |
| 9 | Male | 45 | | | X |
| 10 | Female | 49 | | | X |
| 11 | Female | 72 | | | X |
| 12 | Male | 58 | | | X |
| 13 | Male | 33 | | | X |
| 14 | Female | 64 | | | X |
| 15 | Female | 78 | | | X |
| 16 | Female | 79 | | | X |
| 17 | Male | 61 | | | X |
| 18 | Male | 69 | | | X |
| 19 | Female | 78 | | | X |
| 20 | Female | 71 | | | X |
| 21 | Female | 60 | | | X |
| 22 | Male | 56 | | | X |

Example 2: Sample Preparation

Tissue Preparation

For pathological examination and immunohistochemical staining non-tumorous liver tissue and CCC tumour tissue were fixed in buffered formalin and paraffin embedded. For the proteomics studies the samples were placed on ice immediately after the biopsy, snap-frozen and stored at −80° C. Protein extraction was performed by sonication (6×10 s pulses on ice) in sample buffer (30 mM Tris-HCl; 2 M thiourea; 7 M urea; 4% CHAPS, pH 8.5) and subsequent centrifugation (15000 g, 5 min). The supernatant was collected and the protein concentration was determined by Bio-Rad Protein Assay (Bio-Rad, Hercules, USA).

Example 3: 2D-DIGE Analysis

Example 3.1: Protein Labelling

For 2D-DIGE experiments a minimal labelling using 400 pmol cyanine dyes (GE Healthcare, Munich, Germany) per 50 µg of protein was performed according to the manufacturer's instructions. To avoid biases tumorous and non-tumorous samples were dyed randomly with Cy3 and Cy5. A mixture of all samples was labelled with Cy2 to be used as an internal standard.

Example 3.2: 2D Electrophoresis

For 2D-DIGE experiments the appropriate Cy3- and Cy5-labelled sample pairs from each patient were mixed adding the internal standard (ratio 1:1:1). The isoelectric focusing (IEF) and the second dimension SDS-PAGE were performed as described previously[24].

Example 3.3: Image Acquisition and Evaluation

DIGE gels were scanned on a Typhoon 9400 (Amersham Biosciences) at a resolution of 100 µm. Excitation and emission wavelengths for each dye were set according to the manufacturer's recommendations. Images were preprocessed using ImageQuant™ (GE Healthcare, Munich, Germany) before intra-gel spot detection, inter-gel matching and normalisation of spot intensities to the internal standard in DeCyder 2D™ (GE Healthcare, Munich, Germany). A statistical analysis was performed with the Extended Data Analysis tool (EDA) of DeCyder2D™ resulting in a list of proteins meeting the following criteria: (1) protein spot present in at least 70% of all spot maps, (2) student's t-test with false-discovery rate correction≤0.05, (3) average ratio between experimental groups≥1.5. These differentially expressed proteins were extracted from a preparative 2D-gel and identified by MALDI-TOF-MS.

Example 3.4: Digestion and Protein Identification

Protein spots dissected from preparative gels were subjected to in-gel digestion with trypsin (Promega, Madison, Wis.) and the peptides were thereupon extracted from the gel matrix. MALDI-TOF-MS analyses were performed on an UltraFlex™ II instrument (Bruker Daltronics, Bremen, Germany). Protein identifications were done via ProteinScape (ver. 1.3 SR2) (Bruker Daltronics, Bremen, Germany) using the Uniprot database (ver. 3.87) via Mascot (ver. 2.3.0.2) (Matrix Sciences Ltd., London, UK).

Example 4: Label-Free Analysis

Example 4.1: Sample Preparation

In order to concentrate the samples and remove the detergent used for the lysis of the tissue 5 µg protein of each sample were loaded onto a 4-20% SDS-PAGE gel (Bio-Rad® TGX™ precast gels, Bio-Rad, Hercules, USA) and run for 1 min at 300 V. The proteins were stained with Coomassie Brilliant Blue and digested in-gel using trypsin.

The peptides were extracted by sonicating every gel piece twice for 15 min in 20 µl 50% acetonitrile in 0.1% TFA on ice. To remove acetonitrile the supernatants were vacuum centrifuged. The peptide concentration was determined by amino acid analysis on an ACQUITY-UPLC with AccQ Tag Ultra-UPLC column (Waters, Eschborn, Germany) calibrated with Pierce Amino Acid Standard (Thermo Scientific, Bremen, Germany). After rehydrating the samples with 0.1% TFA 350 ng each were subjected to the LC-MS analysis.

Example 4.2: LC-MS/MS Analysis

Label-free MS-based quantification was performed on an Ultimate 3000 RSLCnano system (Dionex, Idstein, Germany) online coupled to an LTQ Orbitrap Elite (Thermo Scientific, Bremen, Germany). For each analysis 350 ng tryptic peptides dissolved in 15 µl 0.1% TFA were injected and pre-concentrated on a trap column (Acclaim® PepMap 100, 300 µm×5 mm, C18, 5 µm, 100 Å) for 7 min with 0.1% TFA at a flow rate of 30 µl/min. The separation was performed on an analytical column (Acclaim® PepMap RSLC, 75 µm×50 cm, nano Viper, C18, 2 µm, 100 Å) with a gradient from 5-40% solvent B over 98 min (solvent A: 0.1% FA, solvent B: 0.1% FA, 84% acetonitrile). The flow rate was set to 400 nl/min and the column oven temperature to 60° C. The MS was operated in a data-dependant mode. Full scan MS spectra were acquired at a resolution of 60,000 in the Orbitrap analyser, while tandem mass spectra of the twenty most abundant peaks were measured in the linear ion trap after peptide fragmentation by collision-induced dissociation.

Example 4.3: Peptide Quantification and Filtering

The ion intensity-based label-free quantification was done by evaluating the LC-MS data with Progenesis LC-MS™ (ver. 4.0.4265.42984, Nonlinear Dynamics Ltd., Newcastle upon Tyne, UK). Therefore, the generated raw files were imported and the most representative LC-MS run was selected as the reference to which the retention times of the precursor masses of all other runs were aligned. From the thereupon created feature list containing m/z values of all eluted peptides only those charged positively 2-, 3- or 4-fold were used for the quantification. To correct experimental variation between the runs—due to differences in ionisation efficiency or the loaded protein quantity, for example—the raw abundances of each feature were normalised. Details regarding the normalisation have been published previously[24]. After this step, the experimental design was set up by grouping the samples into "non-tumorous liver tissue" (controls) and "CCC-tissue".

Example 3.4: Protein Identification

Proteins from LC-MS runs were identified by Proteome Discoverer (ver. 1.3) (Thermo Scientific, Bremen, Germany) searching the UniProt database (Release 2012_02) via Mascot (ver. 2.3.0.2) (Matrix Sciences Ltd., London, UK). The following search parameters were applied: fixed modification propionamide (C), variable modification oxidation (M), tryptic digestion with up to one missed cleavage, precursor ion mass tolerance of 5 ppm and fragment ion mass tolerance of 0.4 Da.

The search results were filtered by a false discovery rate of less than 1% on peptide level before importing the data into Progenesis LC-MS. By doing so, each peptide was matched to a previously quantified feature.

Example 4.5: Protein Quantification and Filtering

For the protein quantification only peptides unique to one protein within the particular experiment were used. These peptides ANOVA p-values and fold changes were used to calculate the significance and the factor of the regulation for each protein. The protein grouping function of Progenesis LC-MS was disabled in this step. Proteins showing a p-value less than 0.05 and a fold-change greater than 1.5 were assumed to be differentially regulated and the lists were filtered accordingly.

Example 5: Analysis of Regulated Proteins

Previously generated lists of differential proteins were processed by Ingenuity Pathway Analysis software (Version 12402621, Ingenuity Systems, ingenuity.com) in order to assign their cellular localisations.

Example 6: Immunohistochemistry

Paraffin embedded 4-µm slides were dewaxed and pretreated in EDTA buffer (pH 9) at 95° C. for 20 min. All immunohistochemical stains were performed with an automated staining device (Dako Autostainer, Glostrup, Denmark). Both, the source of the primary antibodies and the technical staining details of the automatically performed stainings are listed in Table 2. All stains were developed using a Polymer Kit (ZytoChemPlus (HRP), POLHRS-100, Zytomed Systems). Replacement of the various primary antibodies by mouse or rabbit immunoglobulin served as negative controls.

TABLE 2

Antibodies used for immunohistochemical verification.

| Antibody | Clone | Distributor/Product No. | AB dilution, conditions |
|---|---|---|---|
| Tax1BP3 | 4A10/MS | Sigma/WH0030851M1 | 1:200, 60 min. RT |
| Gelsolin | GS-2C4/Ms | Sigma/G4896 | 1:3000, 30 min. RT |
| 14-3-3 sigma | poly/Rb | Imgenex/IMG-6746A | 1:100, 30 min.RT |
| PKM2 | poly/Rb | abcam/ab131021 | 1:4000, 30 min. RT |
| Serpin H1 | M16.10A1/Ms | abcam/ab13510 | 1:12.000, 30 min. RT |
| CLIC1 | 2D4/Ms | Abnova/H00001192-M01 | 1:9000, 30 min. RT |
| APOA4 | 1D6B6, 1D4C11/Ms | abcam/ab81616 | 1:30.000, 30 min. RT |
| PPA1 | poly/Rb | abcam/ab96099 | 1:500, 30 min. RT |
| FABP1 | 2G4/Ms | Acris/AM09011PU-S | 1:15.000, 30 min. RT |
| BHMT | EPR6782/Rb | abcam/ab124992 | 1:100, 30min. RT |

Rb: produced in rabbit;
Ms: produced in mouse.
AB: antibody;
RT: room temperature Example 7: Results After data analysis and statistical evaluation of the proteins which were found to be differentially regulated between the two experimental groups (fold change≥1.5; p-value≤0.05) 15 candidate proteins were chosen for verification by immunohistchemistry in an independent cohort of 14 patients. This confirmed the significant up-regulation of tax1-binding protein 3 (Tax1BP3), gelsolin (GSN), stress-induced phosphoprotein1 (STIP1), 0.4-3-3 protein sigma (SFN), pyruvate kinase isozymes M1/M2 (PKM2), chloride intracellular channel protein 1 (CLIC1), serpin H1, apolipoprotein A-IV (APOA4) and inorganic pyrophosphatase (PPA1) in tumorous cholangiocytes when compared to normal hepatocytes, whereas fatty acid-binding protein 1 (FABP1) and Betaine-homocysteine S-methyltransferase 1 (BHMT) were significantly down-regulated.

9. Blechacz, B. R.; Gores, G. J., Cholangiocarcinoma. Clinics in liver disease 2008, 12, (1), 131-50, ix.
10. Yonglitthipagon, P.; Pairojkul, C.; Bhudhisawasdi, V.; Mulvenna, J.; Loukas, A.; Sripa, B., Proteomics-based identification of alpha-enolase as a potential prognostic marker in cholangiocarcinoma. Clin Biochem 2012, 45, (10-11), 827-34.
11. Yonglitthipagon, P.; Pairojkul, C.; Chamgramol, Y.; Loukas, A.; Mulvenna, J.; Bethony, J.; Bhudhisawasdi, V.; Sripa, B., Prognostic significance of peroxiredoxin 1 and ezrin-radixin-moesin-binding phosphoprotein 50 in cholangiocarcinoma. Hum Pathol 2012, 43, (10), 1719-30.

TABLE 3

Potential biomarker candidates which were chosen for the verification by immunohistochemistry.

| | | Protein | | 2D-DIGE | | Label-free proteomics | | |
| --- | --- | --- | --- | --- | --- | --- | --- | --- |
| Accession No. | SEQ ID No. | Proteinname | Genname | Anova (p) | Fold change | Paired T-test | Fold change | Immunohistochemistry Sensitivity |
| O00299 | 1 | Chloride intracellular channel protein 1 | CLIC1 | $1.86e^{-03}$ | 4.67 | $2.20e^{-03}$ | 2.29 | 64% |
| O14907 | 2 | Tax1-binding protein 3 | TAX1BP3 | | | $3.26e^{-02}$ | 7.73 | 100% |
| P06396 | 3 | Gelsolin | GSN | $1.9e^{-02}$ | 5.83 | $3.02e^{-07}$ | 6.02 | 100% |
| P06727 | 4 | Apolipoprotein A-IV | APOA4 | $2.3e^{-03}$ | 2.27 | $1.75e^{-05}$ | 3.71 | 57% |
| P14618 | 5 | Pyruvate kinase isozymes M1/M2 | PKM2 | $8.3e^{-03}$ | 8.78 | $1.42e^{-09}$ | 7.29 | 86% |
| P26038 | 6 | Moesin | MSN | $6.8e^{-03}$ | 2.47 | | | 36% |
| P31947 | 7 | 14-3-3 protein sigma | SFN | | | $1.82e^{-05}$ | 7.83 | 100% |
| P31948 | 8 | Stress-induced phosphoprotein 1 | STIP1 | $7.5e^{-04}$ | 1.86 | $8.34e^{-05}$ | 1.69 | 100% |
| P50454 | 9 | Serpin H1 | SERPINH1 | | | $1.60e^{-04}$ | 4.15 | 64% |
| Q15181 | 10 | Inorganic pyrophosphatase | PPA1 | $2.5e^{-03}$ | 1.75 | | | 43% |
| P07148 | 11 | Fatty acid-binding protein, liver | FABP1 | $1.9e^{-06}$ | -30.54 | $8.30e^{-10}$ | -21.72 | 100%* |
| P42765 | 12 | 3-ketoacyl-CoA thiolase, mitochondrial | ACAA2 | $2.9e^{-06}$ | -7.95 | $4.93e^{-10}$ | -9.07 | 7%* |
| P54868 | 13 | Hydroxymethylglutaryl-CoA synthase, mitochondrial | HMGCS2 | $4.6e^{-03}$ | -2.67 | $1.04e^{-10}$ | -14.46 | 21%* |
| P80404 | 14 | 4-aminobutyrate aminotransferase, mitochondrial | ABAT | $7.9e^{-06}$ | -5.36 | $1.94e^{-11}$ | -10.01 | 29%* |
| Q93088 | 15 | Betaine-homocysteine S-methyltransferase 1 | BHMT | $4.6e^{-05}$ | -11.94 | $1.23e^{-10}$ | -17.14 | 100%* |

*indicates the sensitivity for detection of hepatocytes.
By Accession No. the proteins can be identified in data bases.
The said "Accession No." of the biomarkers for CCC refers to Table 3 and is correlated SEQ ID No. 1 to 15.

1. Khan, S. A.; Davidson, B. R.; Goldin, R.; Pereira, S. P.; Rosenberg, W. M.; Taylor-Robinson, S. D.; Thillainayagam, A. V.; Thomas, H. C.; Thursz, M. R.; Wasan, H.; British Society of, G., Guidelines for the diagnosis and treatment of cholangiocarcinoma: consensus document. Gut 2002, 51 Suppl 6, VI1-9.
2. Patel, T., Cholangiocarcinoma. Nat Clin Pract Gastroenterol Hepatol 2006, 3, (1), 33-42.
3. Khan, S. A.; Taylor-Robinson, S. D.; Toledano, M. B.; Beck, A.; Elliott, P.; Thomas, H. C., Changing international trends in mortality rates for liver, biliary and pancreatic tumours. J Hepatol 2002, 37, (6), 806-13.
4. Lazaridis, K. N.; Gores, G. J., Cholangiocarcinoma. Gastroenterology 2005, 128, (6), 1655-67.
5. Khan, S. A.; Thomas, H. C.; Davidson, B. R.; Taylor-Robinson, S. D., Cholangiocarcinoma. Lancet 2005, 366, (9493), 1303-14.
6. Demols, A.; Marechal, R.; Deviere, J.; Van Laethem, J. L., The multidisciplinary management of gastrointestinal cancer. Biliary tract cancers: from pathogenesis to endoscopic treatment. Best practice & research. Clinical gastroenterology 2007, 21, (6), 1015-29.
7. Nehls, O.; Gregor, M.; Klump, B., Serum and bile markers for cholangiocarcinoma. Semin Liver Dis 2004, 24, (2), 139-54.
8. Alvaro, D., Serum and bile biomarkers for cholangiocarcinoma. Curr Opin Gastroenterol 2009, 25, (3), 279-84.
12. Srisomsap, C.; Sawangareetrakul, P.; Subhasitanont, P.; Panichakul, T.; Keeratichamroen, S.; Lirdprapamongkol, K.; Chokchaichamnankit, D.; Sirisinha, S.; Svasti, J., Proteomic analysis of cholangiocarcinoma cell line. Proteomics 2004, 4, (4), 1135-44.
13. Morofuji, N.; Ojima, H.; Onaya, H.; Okusaka, T.; Shimada, K.; Sakamoto, Y.; Esaki, M.; Nara, S.; Kosuge, T.; Asahina, D.; Ushigome, M.; Hiraoka, N.; Nagino, M.; Kondo, T., Macrophage-capping protein as a tissue biomarker for prediction of response to gemcitabine treatment and prognosis in cholangiocarcinoma. J Proteomics 2012, 75, (5), 1577-89.
14. Sriwanitchrak, P.; Viyanant, V.; Chaijaroenkul, W.; Srivatanakul, P.; Gram, H. R.; Eursiddhichai, V.; Na-Bangchang, K., Proteomics analysis and evaluation of biomarkers for detection of cholangiocarcinoma. Asian Pac J Cancer Prev 2011, 12, (6), 1503-10.
15. Wang, X; Dai, S.; Zhang, Z.; Liu, L.; Wang, J.; Xiao, X.; He, D.; Liu, B., Characterization of apolipoprotein A-I as a potential biomarker for cholangiocarcinoma. Eur J Cancer Care (Engl) 2009, 18, (6), 625-35.
16. Metzger, J.; Negm, A. A.; Plentz, R. R.; Weismuller, T. J.; Wedemeyer, J.; Karlsen, T. H.; Dakna, M.; Mullen, W.; Mischak, H.; Manns, M. P.; Lankisch, T. O., Urine proteomic analysis differentiates cholangiocarcinoma from primary sclerosing cholangitis and other benign biliary disorders. Gut 2013, 62, (1), 122-30.

17. Lankisch, T. O.; Metzger, J.; Negm, A. A.; Vosskuhl, K.; Schiffer, E.; Siwy, J.; Weismuller, T. J.; Schneider, A. S.; Thedieck, K.; Baumeister, R.; Zurbig, P.; Weissinger, E. M.; Manns, M. P.; Mischak, H.; Wedemeyer, J., Bile proteomic profiles differentiate cholangiocarcinoma from primary sclerosing cholangitis and choledocholithiasis. Hepatology 2011, 53, (3), 875-84.
18. Farid, S. G.; Craven, R. A.; Peng, J.; Bonney, G. K.; Perkins, D. N.; Selby, P. J.; Rajendra Prasad, K.; Banks, R. E., Shotgun proteomics of human bile in hilar cholangiocarcinoma. Proteomics 2011, 11, (10), 2134-8.
19. Shen, J.; Wang, W.; Wu, J.; Feng, B.; Chen, W.; Wang, M.; Tang, J.; Wang, F.; Cheng, F.; Pu, L.; Tang, Q.; Wang, X.; Li, X., Comparative proteomic profiling of human bile reveals SSP411 as a novel biomarker of cholangiocarcinoma. PLoS One 2012, 7, (10), e47476.
20. Darby, I. A.; Vuillier-Devillers, K.; Pinault, E.; Sarrazy, V.; Lepreux, S.; Balabaud, C.; Bioulac-Sage, P.; Desmouliere, A., Proteomic analysis of differentially expressed proteins in peripheral cholangiocarcinoma. Cancer microenvironment: official journal of the International Cancer Microenvironment Society 2010, 4, (1), 73-91.
21. Jeon, Y. E.; Lee, S. C.; Paik, S. S.; Lee, K. G.; Gin, S. Y.; Kim, H. R.; Yoo, C. W.; Park, H. M.; Han, S. Y.; Choi, D. H.; Kim, H. K., Histology-directed matrix-assisted laser desorption/ionization analysis reveals tissue origin and p53 status of primary liver cancers. Pathology international 2011, 61, (8), 449-55.
22. Scarlett, C. J.; Saxby, A. J.; Nielsen, A.; Bell, C.; Samra, J. S.; Hugh, T.; Baxter, R. C.; Smith, R. C., Proteomic profiling of cholangiocarcinoma: diagnostic potential of SELDI-TOF MS in malignant bile duct stricture. Hepatology 2006, 44, (3), 658-66.
23. Kawase, H.; Fujii, K.; Miyamoto, M.; Kubota, K. C.; Hirano, S.; Kondo, S.; Inagaki, F., Differential LC-MS-based proteomics of surgical human cholangiocarcinoma tissues. J Proteome Res 2009, 8, (8), 4092-103.
24. Megger, D. A.; Bracht, T.; Kohl, M.; Ahrens, M.; Naboulsi, W.; Weber, F.; Hoffmann, A. C.; Stephan, C.; Kuhlmann, K.; Eisenacher, M.; Schlaak, J. F.; Baba, H. A.; Meyer, H. E.; Sitek, B., Proteomic Differences Between Hepatocellular Carcinoma and Nontumorous Liver Tissue Investigated by a Combined Gel-based and Label-free Quantitative Proteomics Study. Mol Cell Proteomics 2013, 12, (7), 2006-20.
25. Kohl, M.; Megger, B. A.; Trippler, M.; Meckel, H.; Ahrens, M.; Bracht, T.; Weber, F.; Hoffmann, A. C.; Baba, H. A.; Sitek, B.; Schlaak, J. F.; Meyer, H. E.; Stephan, C.; Eisenacher, M., A practical data processing workflow for multi-OMICS projects. Biochim Biophys Acta 2013.
26. Sahadevan, S.; Hofmann-Apitius, M.; Schellander, K.; Tesfaye, D.; Fluck, J.; Friedrich, C. M., Text mining in livestock animal science: introducing the potential of text mining to animal sciences. J Anim Sci 2012, 90, (10), 3666-76.
27. Sahadevan, J.; Srinivasan, D., Treatment of obstructive sleep apnea in patients with cardiac arrhythmias. Current treatment options in cardiovascular medicine 2012, 14, (5), 520-8.
28. Kanamori, M.; Sandy, P.; Marzinotto, S.; Benetti, R.; Kai, C.; Hayashizaki, Y.; Schneider, C.; Suzuki, H., The PDZ protein tax-interacting protein-1 inhibits beta-catenin transcriptional activity and growth of colorectal cancer cells. J Biol Chem 2003, 278, (40), 38758-64.
29. Novarino, G.; Fabrizi, C.; Tonini, R.; Denti, M. A.; Malchiodi-Albedi, F.; Lauro, G. M.; Sacchetti, B.; Paradisi, S.; Ferroni, A.; Curmi, P. M.; Breit, S. N.; Mazzanti, M., Involvement of the intracellular ion channel CLIC1 in microglia-mediated beta-amyloid-induced neurotoxicity. J Neurosci 2004, 24, (23), 5322-30.
30. Valenzuela, S. M.; Mazzanti, M.; Tonini, R.; Qiu, M. R.; Warton, K.; Musgrove, E. A.; Campbell, T. J.; Breit, S. N., The nuclear chloride ion channel NCC27 is involved in regulation of the cell cycle. J Physiol 2000, 529 Pt 3, 541-52.
31. Chen, C. D.; Wang, C. S.; Huang, Y. H.; Chien, K. Y.; Liang, Y.; Chen, W. J.; Lin, K. H., Overexpression of CLIC1 in human gastric carcinoma and its clinicopathological significance. Proteomics 2007, 7, (1), 155-67.
32. Petrova, D. T.; Asif, A. R.; Armstrong, V. W.; Dimova, I.; Toshev, S.; Yaramov, N.; Oellerich, M.; Toncheva, D., Expression of chloride intracellular channel protein 1 (CLIC1) and tumor protein D52 (TPD52) as potential biomarkers for colorectal cancer. Clin Biochem 2008, 41, (14-15), 1224-36.
33. Megger, D. A.; Bracht, T.; Meyer, H. E.; Sitek, B., Label-free quantification in clinical proteomics. Biochim Biophys Acta 2013, 1834, (8), 1581-90.
34. Han, M.; Wang, H.; Zhang, H. T.; Han, Z., The PDZ protein TIP-1 facilitates cell migration and pulmonary metastasis of human invasive breast cancer cells in athymic mice. Biochem Biophys Res Commun 2012, 422, (1), 139-45.
35. Han, M.; Wang, H.; Zhang, H. T.; Han, Z., Expression of Tax-interacting protein 1 (TIP-1) facilitates angiogenesis and tumor formation of human glioblastoma cells in nude mice. Cancer Lett 2013, 328, (1), 55-64.
36. Huang, L. R.; Coughtrie, M. W.; Hsu, H. C., Down-regulation of dehydroepiandrosterone sulfotransferase gene in human hepatocellular carcinoma. Mol Cell Endocrinol 2005, 231, (1-2), 87-94.
37. Sundaram, M.; Yao, Z., Intrahepatic role of exchangeable apolipoproteins in lipoprotein assembly and secretion. Arterioscler Thromb Vasc Biol 2012, 32, (5), 1073-8.
38. Abulaizi, M.; Tomonaga, T.; Satoh, M.; Sogawa, K.; Matsushita, K.; Kodera, Y.; Obul, J.; Takano, S.; Yoshitomi, H.; Miyazaki, M.; Nomura, F., The application of a three-step proteome analysis for identification of new biomarkers of pancreatic cancer. Int J Proteomics 2011, 2011, 628787.
39. Dieplinger, H.; Ankerst, D. P.; Burges, A.; Lenhard, M.; Lingenhel, A.; Fineder, L.; Buchner, H.; Stieber, P., Afamin and apolipoprotein A-IV: novel protein markers for ovarian cancer. Cancer Epidemiol Biomarkers Prev 2009, 18, (4), 1127-33.
40. Wang, L. N.; Tong, S. W.; Hu, H. D.; Ye, F.; Li, S. L.; Ren, H.; Zhang, D. Z.; Xiang, R.; Yang, Y. X., Quantitative proteome analysis of ovarian cancer tissues using a iTRAQ approach. J Cell Biochem 2012, 113, (12), 3762-72.
41. Tomonaga, T.; Matsushita, K.; Yamaguchi, S.; Oh-Ishi, M.; Kodera, Y.; Maeda, T.; Shimada, H.; Ochiai, T.; Nomura, F., Identification of altered protein expression and post-translational modifications in primary colorectal cancer by using agarose two-dimensional gel electrophoresis. Clin Cancer Res 2004, 10, (6), 2007-14.
42. Kuroda, Y.; Aishima, S.; Taketomi, A.; Nishihara, Y.; Iguchi, T.; Taguchi, K.; Maehara, Y.; Tsuneyoshi, M., 14-3-3 sigma negatively regulates the cell cycle, and its down-regulation is associated with poor outcome in intrahepatic cholangiocarcinoma. Hum Pathol 2007, 38, (7), 1014-22,
43. Schaap, F. G.; Binas, B.; Danneberg, H.; van der Vusse, G. J.; Glatz, J. F., Impaired long-chain fatty acid utilization by cardiac myocytes isolated from mice lacking the heart-type fatty acid binding protein gene. Circ Res 1999, 85, (4), 329-37.
44. Domingo, M.; Einig, C.; Eigenbrodt, E.; Reinacher, M., Immunohistological demonstration of pyruvate kinase isoenzyme type L in rat with monoclonal antibodies. J Histochem Cytochem 1992, 40, (5), 665-73.
45. Steinberg, P.; Kiingelhoffer, A.; Schafer, A.; Wust, G.; Weisse, G.; Oesch, F.; Eigenbrodt, E., Expression of pyruvate kinase M2 in preneoplastic hepatic foci of N-nitrosomorpholine-treated rats. Virchows Arch 1999, 434, (3), 213-20.
46. Rodriguez-Horche, P.; Luque, J.; Perez-Artes, E.; Pineda, M.; Pinilla, M., Comparative kinetic behaviour and regulation by fructose-1, 6-bisphosphate and ATP of pyruvate kinase from erythrocytes, reticulocytes and bone marrow cells. Comparative biochemistry and physiology. B, Comparative biochemistry 1987, 87, (3), 553-7.
47. Carbonell, J.; Feliu, J. E.; Marco, R.; Sols, A., Pyruvate kinase. Classes of regulatory isoenzymes in mammalian tissues. Eur J Biochem 1973, 37, (1), 148-56.
48. Reinacher, M.; Eigenbrodt, E.; Schering, B.; Schoner, W., Immunohistochemical localization of pyruvate kinase isoenzymes in chicken tissues. Histochemistry 1979, 64, (2), 145-61.
49. Yamada, K.; Noguchi, T., Regulation of pyruvate kinase M gene expression. Biochem Biophys Res Commun 1999, 256, (2), 257-62.
50. Reinacher, M.; Eigenbrodt, E., Immunohistological demonstration of the same type of pyruvate kinase isoenzyme (M2-Pk) in tumors of chicken and rat. Virchows Archiv. B, Cell pathology including molecular pathology 1981, 37, (1), 79-88.
51. Staal, G. E.; Rijksen, G., The role of red cell aging in the diagnosis of glycolytic enzyme defects. Adv Exp Med Biol 1991, 307, 239-49.
52. Chen, M.; Zhang, J.; Manley, J. L., Turning on a fuel switch of cancer: hnRNP proteins regulate alternative splicing of pyruvate kinase mRNA. Cancer Res 2010, 70, (22), 8977-80.
53. Hacker, H. J.; Steinberg, P.; Bannasch, P., Pyruvate kinase isoenzyme shift from L-type to M2-type is a late event in hepatocarcinogenesis induced in rats by a choline-deficient/DL-ethionine-supplemented diet. Carcinogenesis 1998, 19, (1), 99-107.
54. Hogan, B. L.; Barlow, D. P.; Kurkinen, M., Reichert's membrane as a model for studying the biosynthesis and assembly of basement membrane components. Ciba Foundation symposium 1984, 108, 60-74.
55. Kurkinen, M.; Taylor, A.; Garrels, J. I.; Hogan, B. L., Cell surface-associated proteins which bind native type IV collagen or gelatin. J Biol Chem 1984, 259, (9), 5915-22.
56. Razzaque, M. S.; Taguchi, T., Collagen-binding heat shock protein (HSP) 47 expression in anti-thymocyte serum (ATS)-induced glomerulonephritis. J Pathol 1997, 183, (1), 24-9.
57. Razzaque, M. S.; Nazneen, A.; Taguchi, T., Immunolocalization of collagen and collagen-binding heat shock protein 47 in fibrotic lung diseases. Mod Pathol 1998, 11, (12), 1183-8.
58. Masuda, H.; Fukumoto, M.; Hirayoshi, K.; Nagata, K., Coexpression of the collagen-binding stress protein HSP47 gene and the alpha 1(I) and alpha 1(III) collagen genes in carbon tetrachloride-induced rat liver fibrosis. J Clin Invest 1994, 94, (6), 2481-8.
59. Kawada, N.; Kuroki, T.; Kobayashi, K.; Inoue, M.; Nakatani, K.; Kaneda, K.; Nagata, K., Expression of heat-shock protein 47 in mouse liver. Cell Tissue Res 1996, 284, (2), 341-6.
60. Maitra, A.; Iacobuzio-Donahue, C.; Rahman, A.; Sohn, T. A.; Argani, P.; Meyer, R.; Yeo, C. J.; Cameron, J. L.; Goggins, M.; Kern, S. E.; Ashfaq, R.; Hruban, R. H.; Wilentz, R. E., Immunohistochemical validation of a novel epithelial and a novel stromal marker of pancreatic ductal adenocarcinoma identified by global expression microarrays: sea urchin fascin homolog and heat shock protein 47. Am J Clin Pathol 2002, 118, (1), 52-9.
61. Uozaki, H.; Ishida, T.; Kakiuchi, C.; Horiuchi, H.; Gotoh, T.; Iijima, T.; Imamura, T.; Machinami, R., Expression of heat shock proteins in osteosarcoma and its relationship to prognosis. Pathol Res Pract 2000, 196, (10), 665-73.
62. Araki, K.; Mikami, T.; Yoshida, T.; Kikuchi, M.; Sato, Y.; Oh-ishi, M.; Kodera, Y.; Maeda, T.; Okayasu, I., High expression of HSP47 in ulcerative colitis-associated carcinomas: proteomic approach. Br J Cancer 2009, 101, (3), 492-7.
63. Averaimo, S.; Milton, R. H.; Duchen, M. R.; Mazzanti, M., Chloride intracellular channel 1 (CLIC1): Sensor and effector during oxidative stress. FEES Lett 2010, 584, (10), 2076-84.
64. Blanc, J. F.; Lalanne, C.; Plomion, C.; Schmitter, J. M.; Bathany, K.; Gion, J. M.; Bioulac-Sage, P.; Balabaud, C.; Bonneu, M.; Rosenbaum, J., Proteomic analysis of differentially expressed proteins in hepatocellular carcinoma developed in patients with chronic viral hepatitis C. Proteomics 2005, 5, (14), 3778-89.
65. Huang, J. S.; Chao, C. C.; Su, T. L.; Yeh, S. H.; Chen, D. S.; Chen, C. T.; Chen, P. J.; Jou, Y. S., Diverse cellular transformation capability of overexpressed genes in human hepatocellular carcinoma. Biochem Biophys Res Commun 2004, 315, (4), 950-8.
66. Green, P. H.; Glickman, R. M.; Riley, J. W.; Quinet, E., Human apolipoprotein A-IV. Intestinal origin and distribution in plasma. J Clin Invest 1980, 65, (4), 911-9.
67. Fairchild, T. A.; Patejunas, G., Cloning and expression profile of human inorganic pyrophosphatase. Biochim Biophys Acta 1999, 1447, (2-3), 133-6.
68. Lexander, H.; Palmberg, C.; Auer, G.; Hellstrom, M.; Franzen, B.; Jornvall, H.; Egevad, L., Proteomic analysis of protein expression in prostate cancer. Anal Quant Cytol Histol 2005, 27, (5), 263-72.
69. Jeong, S. H.; Ko, G. H.; Cho, Y. H.; Lee, Y. J.; Cho, B. I.; Ha, W. S.; Choi, S. K.; Kim, J. W.; Lee, C. W.; Heo, Y. S.; Shin, S. H.; Yoo, J.; Hong, S. C., Pyrophosphatase overexpression is associated with cell migration, invasion, and poor prognosis in gastric cancer. Tumour Biol 2012, 33, (6), 1889-98.
70. Pelsers, M. M.; Morovat, A.; Alexander, G. J.; Hermens, W. T.; Trull, A. K.; Glatz, J. F., Liver fatty acid-binding protein as a sensitive serum marker of acute hepatocellular damage in liver transplant recipients. Clin Chem 2002, 48, (11), 2055-7.
71. Pelsers, M. M.; Namiot, Z.; Kisielewski, W.; Namiot, A.; Januszkiewicz, M.; Hermens, W. T.; Glatz, J. F., Intestinal-type and liver-type fatty acid-binding protein in the intestine. Tissue distribution and clinical utility. Clin Biochem 2003, 36, (7), 529-35.
72. Gordon, J. I.; Elshourbagy, N.; Lowe, J. B.; Liao, W. S.; Alpers, D. H.; Taylor, J. M., Tissue specific expression and developmental regulation of two genes coding for rat fatty acid binding proteins. J Biol Chem 1985, 260, (4), 1995-8.
73. Shields, H. M.; Bates, M. L.; Bass, N. M.; Best, C. J.; Alpers, D. H.; Ockner, R. K., Light microscopic immunocytochemical localization of hepatic and intestinal types of fatty acid-binding proteins in rat small intestine. J Lipid Res 1986, 27, (5), 549-57.
74. Maatman, R. G.; Van Kuppevelt, T. H.; Veerkamp, J. H., Two types of fatty acid-binding protein in human kidney. Isolation, characterization and localization. Biochem J 1991, 273 (Pt 3), 759-66.
75. Noiri, E.; Doi, K.; Negishi, K.; Tanaka, T.; Hamasaki, Y.; Fujita, T.; Portilla, D.; Sugaya, T., Urinary fatty acid-binding protein 1: an early predictive biomarker of kidney injury. Am J Physiol Renal Physiol 2009, 296, (4), F669-79.
76. Delgado-Reyes, C. V.; Wallig, M. A.; Garrow, T. A., Immunohistochemical detection of betaine-homocysteine S-methyltransferase in human, pig, and rat liver and kidney. Arch Biochem Biophys 2001, 393, (1), 184-6.
77. Garrow, T. A., Purification, kinetic properties, and cDNA cloning of mammalian betaine-homocysteine methyltransferase. J Biol Chem 1996, 271, (37), 22831-8.
78. Avila, M. A.; Berasain, C.; Torres, L.; Martin-Duce, A.; Corrales, F. J.; Yang, H.; Prieto, J.; Lu, S. C.; Caballeria, J.; Rodes, J.; Matoe, J. M., Reduced mRNA abundance of the main enzymes involved in methionine metabolism in human liver cirrhosis and hepatocellular carcinoma. J Hepatol 2000, 33, (6), 907-14.
79. Liang, C. R.; Leow, C. K.; Neo, J. C.; Tan, G. S.; Lo, S. L.; Lim, J. W.; Seow, T. K.; Lai, P. B.; Chung, M. C., Proteome analysis of human hepatocellular carcinoma tissues by two-dimensional difference gel electrophoresis and mass spectrometry. Proteomics 2005, 5, (8), 2258-71.
80. Sun, W.; Xing, B.; Sun, Y.; Du, X.; Lu, M.; Hao, C.; Lu, Z.; Mi, W.; Wu, S.; Wei, H.; Gao, X.; Zhu, Y.; Jiang, Y.; Qian, X.; He, F., Proteome analysis of hepatocellular carcinoma by two-dimensional difference gel electrophoresis: novel protein markers in hepatocellular carcinoma tissues. Mol Cell Proteomics 2007, 6, (10), 1798-808.

The invention claimed is:

1. A method for identifying biomarkers for cholangiocellular carcinoma (CCC), comprising:
    a) collecting tumorous tissue samples and non-tumorous tissue samples from at least 5 patients with CCC;
    b) comparing the tumorous tissue samples with the non-tumorous tissue samples by two-dimensional differential in-gel electrophoresis (2D-DIGE) and thereby identifying a first set of biomarker candidates for CCC showing different expression in tumorous tissue and non-tumorous tissue determined by statistical analysis;
    c) comparing the tumorous tissue samples with the non-tumorous tissue samples by label-free liquid chromatography-mass spectrometry (LC-MS) and thereby identifying a second set of biomarker candidates for CCC showing different expression in tumorous tissue and non-tumorous tissue determined by statistical analysis;
    d) comparing the first set of biomarker candidates obtained by 2D-DIGE according to step b) with the second set of biomarker candidates obtained by label-free LC-MS according to step c) and thereby identifying a third set of biomarker candidates for CCC showing different expression with both 2D-DIGE and label-free LC MS; and
    e) performing an immunohistochemical analysis of the third set of biomarker candidates for CCC identified from step d) by comparing the expression of a respective biomarker candidate in the tumorous tissue of a subject with the expression of said respective biomarker candidate in non-tumorous tissue of the same subject and selecting one or more biomarkers for CCC that display a sensitivity of 40% or more.

2. The method of claim 1,
    wherein the one or more biomarkers for CC selected from step e) are:
    a) proteins found to be up-regulated in the tumorous tissue and are useful for the detection of CCC tumour cells; or
    b) proteins found to be down-regulated in the tumorous tissue and are useful for the detection of hepatocytes.

3. The method of claim 1, wherein the one or more biomarkers for CCC selected from step e) comprises chloride intracellular channel protein 1, Tax1-binding protein 3, gelsolin, apolipoprotein A-IV, pyruvate kinase isoenzymes M1/M2, moesin, 14-3-3 protein sigma, stress-induced phosphoprotein 1, serpin H1, inorganic pyrophosphatase, fatty acid-binding protein (liver), 3-ketoacyl-CoA thiolase (mitochondrial), hydroxymethylglutaryl-CoA synthase (mitochondrial), 4-aminobutyrate aminotransferase (mitochondrial), betaine-homocysteine S-methyltransferase 1, or partial sequences or homologues of these proteins.

4. The method of claim 1, wherein the subject from which the tumorous tissue and the non-tumorous tissue are used for the immunohistochemical analysis of step e) is different from the at least 5 patients with CCC from which the tumorous tissue samples and the non-tumorous tissue samples are collected in step a).

* * * * *